United States Patent
Nakagawa et al.

(10) Patent No.: US 8,808,928 B2
(45) Date of Patent: Aug. 19, 2014

(54) FUEL CELL, METHOD FOR OPERATING THE SAME, AND ELECTRONIC DEVICE

(75) Inventors: Takaaki Nakagawa, Kanagawa (JP); Hideki Sakai, Kanagawa (JP); Hideyuki Kumita, Kanagawa (JP); Masaya Kakuta, Kanagawa (JP)

(73) Assignee: Sony Corporation, Tokyo (JP)

( * ) Notice: Subject to any disclaimer, the term of this patent is extended or adjusted under 35 U.S.C. 154(b) by 976 days.

(21) Appl. No.: 12/672,582

(22) PCT Filed: Jul. 31, 2008

(86) PCT No.: PCT/JP2008/063737
§ 371 (c)(1),
(2), (4) Date: Feb. 8, 2010

(87) PCT Pub. No.: WO2009/025158
PCT Pub. Date: Feb. 26, 2009

(65) Prior Publication Data
US 2011/0171541 A1    Jul. 14, 2011

(30) Foreign Application Priority Data
Aug. 17, 2007 (JP) ................ P2007-212702

(51) Int. Cl.
H01M 8/16 (2006.01)
H01M 8/04 (2006.01)
H01M 4/60 (2006.01)

(52) U.S. Cl.
USPC ............. 429/401; 429/516; 429/531

(58) Field of Classification Search
USPC ....................... 429/401, 516, 531
See application file for complete search history.

(56) References Cited

U.S. PATENT DOCUMENTS

| | | | |
|---|---|---|---|
| 5,284,645 A * | 2/1994 | Long, Jr. ................. | 424/9.37 |
| 5,910,378 A | 6/1999 | Debe et al. | |
| 2004/0191599 A1* | 9/2004 | Jackson et al. ........... | 429/30 |
| 2005/0053825 A1 | 3/2005 | Sakai et al. | |
| 2005/0158618 A1* | 7/2005 | Liberatore et al. ....... | 429/105 |

(Continued)

FOREIGN PATENT DOCUMENTS

| | | |
|---|---|---|
| JP | 5-502857 | 5/1993 |
| JP | 2000133297 | 5/2000 |

(Continued)

OTHER PUBLICATIONS

Written Opinion of the International Searching Authority, issued on Mar. 9, 2010, for corresponding PCT/JP2008/063737 (11 pages).

(Continued)

*Primary Examiner* — Muhammad Siddiquee
(74) *Attorney, Agent, or Firm* — K&L Gates LLP

(57) ABSTRACT

Provided is a fuel cell having a structure in which a cathode and an anode face each other with a proton conductor therebetween. In this fuel cell, an oxygen reductase or the like is immobilized on at least the cathode, and the cathode is composed of a material having pores therein such as porous carbon. In this fuel cell, the volume of water contained in the cathode is controlled to be 70% or less of the volume of the pores of the cathode, whereby a high current value can be stably obtained through optimization of the amount of moisture contained in the cathode when an enzyme is immobilized on at least the cathode. Also provided is a method for operating the fuel cell.

11 Claims, 21 Drawing Sheets

(56) References Cited

U.S. PATENT DOCUMENTS

| | | | |
|---|---|---|---|
| 2006/0105418 A1 | 5/2006 | Sato et al. | |
| 2007/0062821 A1 | 3/2007 | Sato et al. | |
| 2007/0134520 A1* | 6/2007 | Shimomura et al. | 429/2 |
| 2007/0196722 A1* | 8/2007 | Tomita et al. | 429/43 |
| 2007/0218345 A1* | 9/2007 | Sakai et al. | 429/43 |
| 2007/0224466 A1* | 9/2007 | Nakagawa et al. | 429/13 |
| 2008/0274393 A1* | 11/2008 | Markoski et al. | 429/41 |
| 2009/0011002 A1* | 1/2009 | Zabicky et al. | 424/450 |

FOREIGN PATENT DOCUMENTS

| | | |
|---|---|---|
| JP | 2003282124 | 10/2003 |
| JP | 2004071559 | 3/2004 |
| JP | 2004-521881 | 7/2004 |
| JP | 2005013210 | 1/2005 |
| JP | 2005310613 | 11/2005 |
| JP | 2006024555 | 1/2006 |
| JP | 2006049215 | 2/2006 |
| JP | 2006127957 | 5/2006 |
| JP | 2006156354 | 6/2006 |
| JP | 2007012281 | 1/2007 |
| JP | 2007035437 | 2/2007 |
| JP | 2007087627 | 4/2007 |
| JP | 2007188810 | 7/2007 |
| JP | 2008-60067 | 3/2008 |
| JP | 2006093090 | 4/2010 |
| WO | 91-04664 | 4/1991 |
| WO | 02-48164 | 6/2002 |
| WO | 2005122315 | 12/2005 |
| WO | 2006022224 | 3/2006 |
| WO | WO2006022224 A1 | 3/2006 |
| WO | 2007/088975 A1 | 8/2007 |
| WO | WO2007088975 A1 | 8/2007 |

OTHER PUBLICATIONS

Supplementary European Search Report mailed Jul. 27, 2011, for corresponding European Appln. No. 08828005.2.

International Search Report (PCT/JP2008/063737) dated Oct. 14, 2008.

Japanese Patent Office, Notification of reasons for refusal issued in connection with Japanese Patent Application No. 2007-212702, dated Sep. 11, 2012. (8 pages).

Japanese Office Action issued on Dec. 11, 2012 for corresponding Japanese Appln. No. 2007-212702 (3 pages).

European Office Action issued on Sep. 11, 2012 for corresponding European Appln. No. 08 828 005.2-1227 (5 pages).

* cited by examiner

FIG. 16
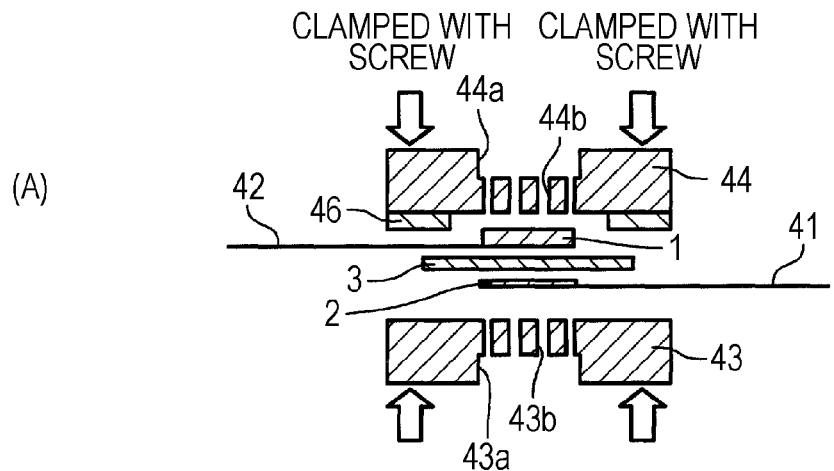
(A)
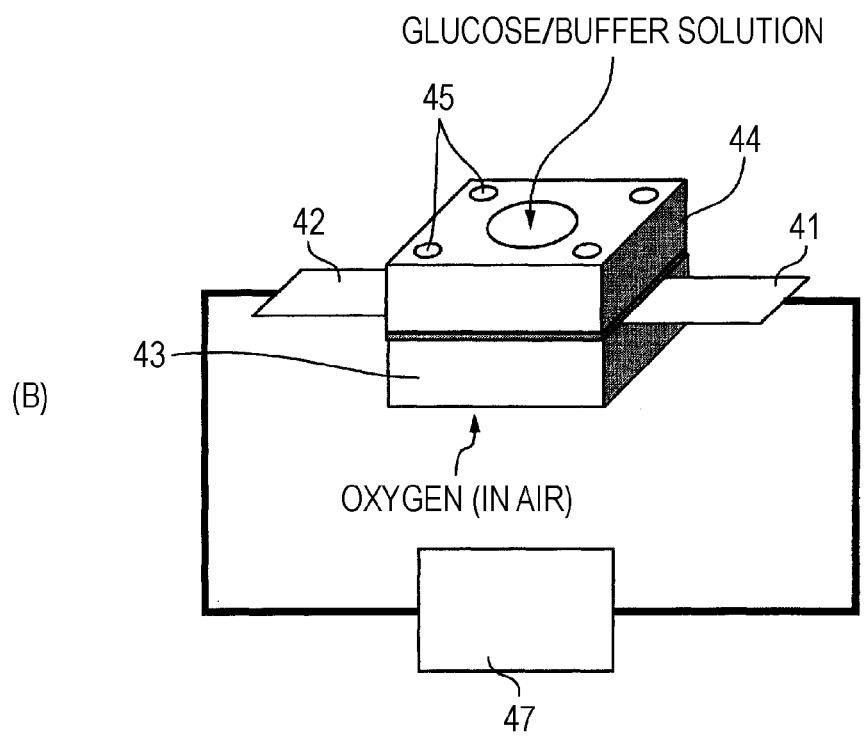
(B)

FIG. 22
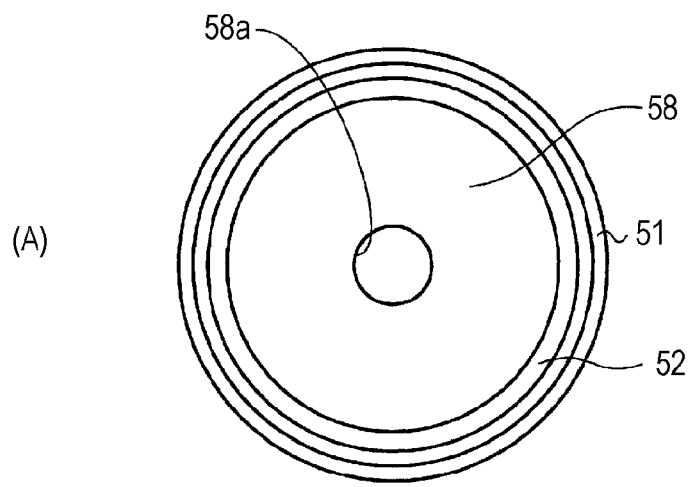
(A)
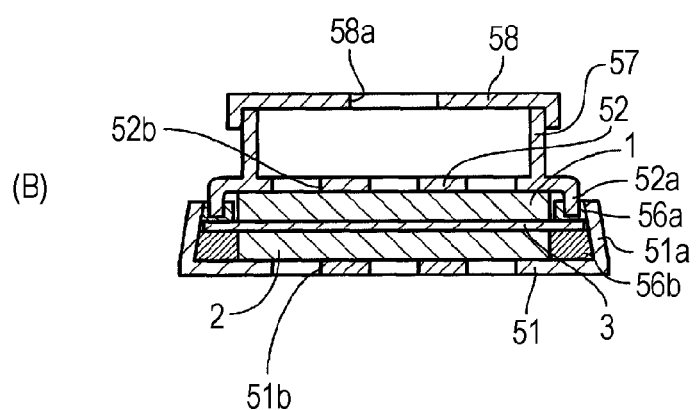
(B)
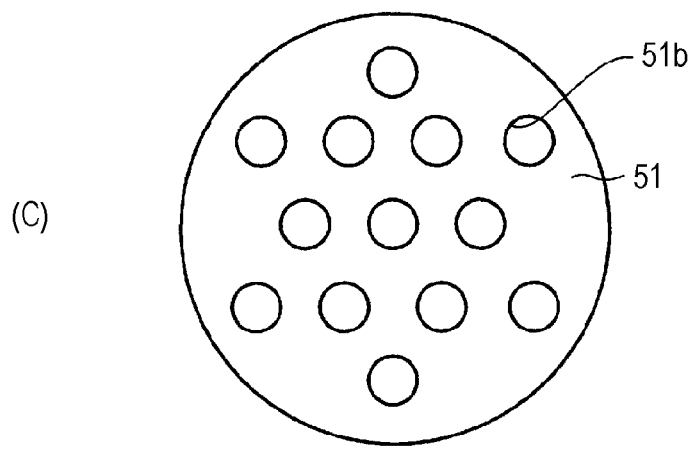
(C)

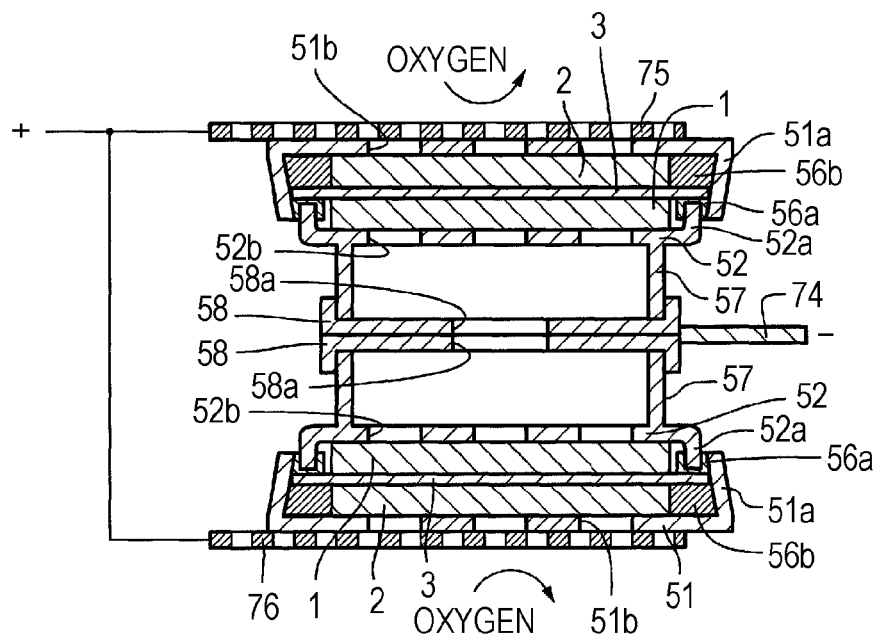

FUEL CELL, METHOD FOR OPERATING THE SAME, AND ELECTRONIC DEVICE

CROSS REFERENCE TO RELATED APPLICATIONS

The present application is a national stage of International Application No. PCT/JP2008/063737 filed on Jul. 31, 2008 and claims priority to Japanese Patent Application No. 2007-212702 filed on Aug. 17, 2007, the disclosures of which are incorporated herein by reference.

BACKGROUND

The present invention relates to a fuel cell in which an enzyme is immobilized on at least a cathode, a method for operating the same, and an electronic device using the fuel cell.

Fuel cells have a structure in which a cathode (oxidizing agent electrode) and an anode (fuel electrode) face each other with an electrolyte (proton conductor) therebetween. In conventional fuel cells, a fuel (hydrogen) supplied to the anode is oxidized and separated into electrons and protons ($H^+$), the electrons are transferred to the anode, and the $H^+$ are moved to the cathode through the electrolyte. On the cathode, the $H^+$ react with oxygen supplied from the outside and electrons sent from the anode through an external circuit to produce water ($H_2O$).

Thus, fuel cells are high-efficiency power-generating devices that directly convert chemical energy possessed by a fuel into electrical energy, and thus chemical energy possessed by energy from a fossil fuel such as natural gas, petroleum, or coal can be extracted as electrical energy regardless of the place or the time of use, and in addition, with a high conversion efficiency. Accordingly, hitherto, research and development of fuel cells for the application to a large-scale power generation or the like has been actively carried out. For example, a fuel cell was installed in a space shuttle, and it was demonstrated that water for the crew can be replenished together with generation of electric power and that the fuel cell is a clean power-generating device.

Furthermore, recently, fuel cells that exhibit a relatively low operation temperature range of room temperature to about 90° C., for example, solid polymer-type fuel cells, have been developed and attracted attention. Consequently, not only large-scale power generation applications but also applications of a fuel cell to a small system such as a power supply for powering automobiles or a portable power supply for a personal computer, a mobile device, or the like have been searched for.

As described above, a wide range of applications ranging from large-scale power generation to small-scale power generation can be expected for fuel cells, and the fuel cells have attracted a lot of attention as power-generating devices with a high efficiency. However, in fuel cells, since natural gas, petroleum, coal, or the like is usually used as a fuel by converting it into hydrogen gas with a reformer, limited resources are consumed, it is necessary to perform heating to a high temperature, and a catalyst composed of an expensive noble metal such as platinum (Pt) is necessary, thus causing various problems. In addition, even in the case where hydrogen gas or methanol is directly used as a fuel, care should be taken in the handling thereof.

Under these circumstances, the fact that the biological metabolism carried out in the living organism is a high-efficiency energy conversion mechanism has been focused and an application of this to a fuel cell has been proposed. The term "biological metabolism" used herein includes aspiration, photosynthesis, and the like carried out in microbial somatic cells. The biological metabolism combines the feature that the power generation efficiency is very high with the feature that a reaction proceeds under a mild condition at about room temperature.

For example, aspiration is a mechanism in which nutrients such as saccharides, fat, and proteins are taken into microbes or cells, the chemical energy thereof is converted into oxidation-reduction energy, i.e., electrical energy, by reducing nicotinamide adenine dinucleotide ($NAD^+$) to reduced nicotinamide adenine dinucleotide (NADH) in a process of producing carbon dioxide ($CO_2$) through a glycolytic pathway and a citric acid (TCA) cycle including a large number of enzyme reaction steps and, furthermore, in an electron transport system, the electrical energy of NADH is directly converted into the electrical energy of a proton gradient and, in addition, oxygen is reduced to produce water. The electrical energy obtained here produces adenosine triphosphate (ATP) from adenosine diphosphate (ADP) with ATP synthase, and this ATP is used for reactions that are necessary for growing microbes or cells. This energy conversion is carried out in the cytosol and mitochondria.

Also, photosynthesis is a mechanism in which water is oxidized to produce oxygen in a process of taking light energy and converting the light energy into electrical energy by reducing nicotinamide adenine dinucleotide phosphate ($NADP^+$) to reduced nicotinamide adenine dinucleotide phosphate (NADPH) through the electron transport system. This electrical energy takes $CO_2$, is used for a carbon-fixation reaction, and is used for synthesis of carbohydrates.

As for a technology to use the above-described biological metabolism for a fuel cell, a microbial cell has been reported, in which electrical energy generated in microbes is taken out of the microbes through an electron mediator and the electron is transferred to an electrode to obtain a current (refer to, for example, Japanese Unexamined Patent Application Publication No. 2000-133297).

However, in microbes and cells, a large number of unnecessary reactions are present besides the target reaction such as conversion of chemical energy to electrical energy. Therefore, in the method described above, electrical energy is consumed in undesired reactions and a sufficient energy conversion efficiency is not achieved.

Under these circumstances, fuel cells (biofuel cells) in which only a desired reaction is conducted by using an enzyme have been proposed (refer to, for example, Japanese Unexamined Patent Application Publication No. 2003-282124, Japanese Unexamined Patent Application Publication No. 2004-71559, Japanese Unexamined Patent Application Publication No. 2005-13210, Japanese Unexamined Patent Application Publication No. 2005-310613, Japanese Unexamined Patent Application Publication No. 2006-24555, Japanese Unexamined Patent Application Publication No. 2006-49215, Japanese Unexamined Patent Application Publication No. 2006-93090, Japanese Unexamined Patent Application Publication No. 2006-127957, Japanese Unexamined Patent Application Publication No. 2006-156354, Japanese Unexamined Patent Application Publication No. 2007-12281, Japanese Unexamined Patent Application Publication No. 2007-35437, and Japanese Unexamined Patent Application Publication No. 2007-87627). In these biofuel cells, a fuel is decomposed by an enzyme to separate into protons and electrons, and biofuel cells in which an alcohol such as methanol or ethanol or a monosaccharide such as glucose is used as the fuel have been developed.

SUMMARY

In general, a material having pores, such as porous carbon, is used as a cathode of the above biofuel cells for the purpose of oxygen supply. However, in the cathode composed of such a material having pores, water produced by reacting $H^+$ supplied from an anode through an electrolyte with oxygen supplied from the outside and electrons sent from the anode through an external circuit and water exuded by the osmotic pressure from the electrolyte containing a buffer solution fill the pores in the cathode. As a result, the inside of the cathode may be submerged in water. When the inside of the cathode is submerged, it becomes difficult to supply oxygen to the cathode. Thus, the current obtained from the biofuel cell is significantly decreased. Therefore, it is important to control the amount of moisture contained in the cathode, but little research has been performed on the amount of moisture contained in the cathode.

Accordingly, an object of the present invention is to provide a fuel cell in which a high current value can be stably obtained through optimization of the amount of moisture contained in a cathode when an enzyme is immobilized on at least the cathode, and a method for operating the same.

Another object of the present invention is to provide an electronic device using the above excellent fuel cell.

To solve the above problem, the inventors of the present invention have conducted extensive studies on the effect of the amount of moisture contained in a cathode on the performance of a fuel cell in the case where en enzyme is immobilized on the cathode and the cathode is composed of a material having pores, such as porous carbon. As a result, the inventors of the present invention have found that a catalytic current value exhibits a specific change due to the amount of moisture contained in the cathode, have found an optimum range of the amount of moisture contained in the cathode on the basis of this finding, and have devised the present invention.

Specifically, in order to solve the above problem, a first invention provides a fuel cell having a structure in which a cathode and an anode face each other with a proton conductor therebetween, wherein an enzyme is immobilized on at least the cathode and the cathode has pores therein, the fuel cell being characterized in that the volume of water contained in the cathode is 70% or less of the volume of the pores of the cathode.

A second invention provides a method for operating a fuel cell having a structure in which a cathode and an anode face each other with a proton conductor therebetween, wherein an enzyme is immobilized on at least the cathode and the cathode has pores therein, the method being characterized in that the volume of water contained in the cathode is controlled to be 70% or less of the volume of the pores of the cathode.

A third invention provides an electronic device including one or a plurality of fuel cells, the electronic device being characterized in that at least one of the fuel cells has a structure in which a cathode and an anode face each other with a proton conductor therebetween, wherein an enzyme is immobilized on at least the cathode and the cathode has pores therein, and the volume of water contained in the cathode is 70% or less of the volume of the pores of the cathode.

In the first to third inventions, the term "volume of water contained in a cathode" means the sum of the volume of water contained in all pores inside the cathode, and the term "volume of pores of a cathode" means the sum of the volume of all pores inside the cathode. The volume of the pores of the cathode is equal to (volume of entire cathode)×(porosity of cathode material). Accordingly, the phrase "the volume of water contained in the cathode is 70% or less of the volume of the pores of the cathode" is represented by (volume of water contained in cathode)/[(volume of entire cathode)×(porosity of cathode material)] 70%. The volume of water contained in the cathode is preferably 60% or less of the volume of the pores of the cathode, and is more than 0%. The form of water contained in the cathode may be a solid or the like, instead of a liquid.

In the first to third inventions, as for the material having pores, the material being used as the cathode, carbon-based materials such as porous carbon, carbon pellets, carbon felt, and carbon paper are often used, but other materials may be used. The same materials can be used as the material for the anode.

Various enzymes can be used as the enzymes immobilized on the cathode and the anode, and the enzymes are selected according to need. In addition, in the case where enzymes are immobilized on the cathode and the anode, preferably, an electron mediator is immobilized in addition to the enzymes.

The enzyme immobilized on the cathode typically includes an oxygen reductase. For example, bilirubin oxidase, laccase, ascorbic acid oxidase, or the like may be used as the oxygen reductase. In such a case, preferably, in addition to the enzyme, an electron mediator is also immobilized on the cathode. As for the electron mediator, for example, potassium hexacyanoferrate, potassium ferricyanide, potassium octacyanotungstate, or the like is used. Preferably, the electron mediator is immobilized at a sufficiently high concentration, for example, $0.64 \times 10^{-6}$ mol/mm$^2$ or more on average.

For example, in the case where a monosaccharide such as glucose is used as a fuel, the enzyme immobilized on the anode includes oxidases that accelerate oxidation of the monosaccharide and decompose the monosaccharide. In general, in addition to this, the enzyme includes a coenzyme oxidase that returns a coenzyme reduced by the oxidase to an oxidized form. Electrons are produced when the coenzyme is retuned to the oxidized form by the action of this coenzyme oxidase, and the electrons are transferred from the coenzyme oxidase to an electrode through an electron mediator. For example, NAD$^+$-dependent glucose dehydrogenase (GDH) is used as the oxidase. For example, nicotinamide adenine dinucleotide (NAD$^+$) is used as the coenzyme. For example, diaphorase is used as the coenzyme oxidase.

In the case where polysaccharides (referring to polysaccharides in a broad sense, referring to all carbohydrates that produce two molecules or more of a monosaccharide through hydrolysis, and including oligosaccharides such as disaccharides, trisaccharides, and tetrasaccharides) are used as a fuel, preferably, a catabolic enzyme that accelerates decomposition, e.g., hydrolysis, of polysaccharides and produces monosaccharides such as glucose is also immobilized in addition to the above-described oxidase, coenzyme oxidase, coenzyme, and electron mediator. Specific examples of polysaccharides include starch, amylose, amylopectin, glycogen, cellulose, maltose, sucrose, and lactose. These are composed of two or more monosaccharides bonded together, and all polysaccharides include glucose as a monosaccharide of a bonding unit. Note that amylose and amylopectin are components contained in starch, and starch is a mixture of amylose and amylopectin. In the case where glucoamylase is used as a catabolic enzyme for polysaccharides and glucose dehydrogenase is used as oxidase for decomposing monosaccharides, power generation can be conducted by using a fuel containing a polysaccharide that can be decomposed to glucose by glucoamylase, for example, any one of starch, amylose, amylopectin, glycogen, and maltose. Note that glucoamylase is a catabolic enzyme that hydrolyzes α-glucan such as starch to produce glucose and glucose dehydrogenase is an oxidase that oxidizes β-D-glucose to D-glucono-δ-lactone. In a preferable configuration, the catabolic enzyme for decomposing a polysaccharide is also immobilized on the anode and the polysaccharide that ultimately functions as a fuel is also immobilized on the anode.

Also, in the case where starch is used as the fuel, a gelled, solidified fuel produced by gelatinizing starch may also be used. In this case, preferably, a method in which gelatinized starch is brought into contact with an anode on which an enzyme and the like have been immobilized or is immobilized on the anode together with the enzyme and the like may be employed. If such an electrode is used, the starch concentration on the surface of the anode can be kept at a level higher than that in the case where starch dissolved in a solution is used, and the rate of decomposition reaction by the enzyme is increased to improve the output. In addition, the handling of the fuel is easier than that in the case of a solution and thus a fuel supply system can be simplified. Furthermore, inhibition of turnover of the fuel cell is not necessary and thus it is very advantageous to use the fuel cell in mobile devices, for example.

Any compound may be basically used as the electron mediator, but compounds having a quinone skeleton, in particular, compounds having a naphthoquinone skeleton are preferably used. Various naphthoquinone derivatives can be used as the compounds having a naphthoquinone skeleton. Specifically, for example, 2-amino-1,4-naphthoquinone (ANQ), 2-amino-3-methyl-1,4-naphthoquinone (AMNQ), 2-methyl-1,4-naphthoquinone (VK3), 2-amino-3-carboxy-1,4-naphthoquinone (ACNQ), and the like are used. As for the compounds having a quinone skeleton, for example, anthraquinone and derivatives thereof can also be used besides the compounds having a naphthoquinone skeleton. The electron mediator may contain one type or two or more types of other compounds serving as the electron mediator, if necessary, besides the compounds having a quinone skeleton. As for a solvent used when a compound having a quinone skeleton, in particular, a compound having a naphthoquinone skeleton is immobilized on the anode, acetone is preferably used. By using acetone as a solvent in this manner, the solubility of the compound having a quinone skeleton can be increased, and the compound having a quinone skeleton can be efficiently immobilized on the anode. The solvent may contain one or two or more solvents other than acetone, as required.

In one example, 2-methyl-1,4-naphthoquinone (VK3) serving as the electron mediator, reduced nicotinamide adenine dinucleotide (NADH) serving as the coenzyme, glucose dehydrogenase serving as the oxidase, and diaphorase serving as the coenzyme oxidase are immobilized on the anode. Preferably, they are immobilized at a ratio of 1.0 (mol):0.33 to 1.0 (mol):(1.8 to 3.6)×$10^6$ (U):(0.85 to 1.7)×$10^7$ (U). Here, U (unit) is an index indicating the enzyme activity and represents a degree of reaction of 1 μmol of substrate per minute at a specific temperature and pH.

Various materials can be used as an immobilizing material to immobilize the enzyme, coenzyme, electron mediator, and the like on the anode and the cathode. Preferably, polyion complexes formed by using a polycation such as poly-L-lysine (PLL) or a salt thereof and a polyanion such as polyacrylic acid (for example, sodium polyacrylate (PAAcNa)) or a salt thereof can be used. The polyion complex can be configured so that the enzyme, coenzyme, electron mediator, and the like can be contained inside thereof.

Meanwhile, in the case where electron mediators are immobilized on the cathode and the anode of this fuel cell, since the electron mediators usually have low molecular weights, it is not always easy to completely suppress elution and to maintain a state in which the electron mediators are immobilized on the cathode and the anode for a long time. Therefore, an electron mediator used in the cathode can be moved to the anode side, whereas an electron mediator used in the anode can be moved to the cathode side. In such a case, a decrease in the output of the fuel cell and a decrease in the capacitance may be caused. In order to eliminate this problem, it is effective to use an electrolyte with an electric charge having the same sign as the electric charge of an oxidized form or a reduced form of the electron mediator. In this case, a repulsive force acts between the electric charge of the electrolyte and the electric charge of the oxidized form or the reduced form of the electron mediator. Consequently, the electron mediator does not tend to move to the electrolyte side, thus effectively suppressing the movement of the electron mediator to the opposite side through the electrolyte. Typically, when the electrolyte contains a polymer with an electric charge having the same sign as the electric charge of the oxidized form or the reduced form of the electron mediator, e.g., a polyanion or a polycation, the electrolyte has an electric charge having the same sign as the electric charge of the oxidized form or the reduced form of the electron mediator, but the method is not limited to this. Other methods may be employed so that the electrolyte has an electric charge having the same sign as the electric charge of the oxidized form or the reduced form of the electron mediator. Specifically, in the case where an oxidized form or a reduced form of an electron mediator used in at least one of the cathode and the anode has a negative electric charge, the electrolyte is configured to contain a polymer having a negative electric charge, e.g., a polyanion. In the case where an oxidized form or a reduced form of an electron mediator has a positive electric charge, the electrolyte is configured to contain a polymer having a positive electric charge, e.g., a polycation. As the polyanion, for example, besides Nafion (trade name, DuPont, USA), which is an ion-exchange resin having a fluorine-containing carbon sulfonic acid group, dichromate ion ($Cr_2O_7^{2-}$), paramolybdate ion ($[Mo_7O_{24}]^{6-}$), polyacrylic acid (for example, sodium polyacrylate (PAAcNa)), or the like can be used. As the polycation, for example, poly-L-lysine (PLL) or the like can be used.

On the other hand, the inventors of the present invention have found a phenomenon that the output of a fuel cell can be markedly improved by immobilizing a phospholipid such as dimyristoylphosphatidylcholine (DMPC) on the anode in addition to the enzyme and the electron mediator. That is, it was found that such a phospholipid functions as an agent for increasing the output. Various studies were conducted on the reason why the output can be increased by immobilizing a phospholipid as described above, and the following conclusions were obtained. One of the reasons why a satisfactorily large output is not obtained from a conventional fuel cell is that the enzyme and the electron mediator immobilized on the anode are not homogeneously mixed and the two are in a state of being aggregated separately from each other. However, the enzyme and the electron mediator can be prevented from being aggregated separately from each other by immobilizing a phospholipid, and thus the enzyme and the electron mediator can be homogeneously mixed. Furthermore, the reason why the enzyme and the electron mediator can be homogeneously mixed by the addition of the phospholipid was investigated, and a very rare phenomenon was found in which the diffusion coefficient of the reduced form of the electron mediator is significantly increased by the addition of the phospholipid. That is, it was found that the phospholipid functions as an electron mediator diffusion accelerator. This effect of immobilization of the phospholipid is particularly significant in the case where the electron mediator is a compound having a quinine skeleton. A similar effect can also be achieved in the case where phospholipid derivatives or polymers of phospholipids or derivatives thereof are used instead of phospholipids. It should be noted that, most generally, the agent for increasing the output refers to an agent capable of increasing the rate of reaction at the electrode on which the enzyme and the electron mediator are immobilized and increasing the output. In addition, most generally, the electron mediator diffusion accelerator refers to an agent for increasing the diffusion coefficient of the electron mediator in the inside of the electrode on which the enzyme and the electron mediator are immobilized or maintaining or increasing the concentration of the electron mediator in the vicinity of the electrode.

As for the proton conductor, various substances can be used and selected according to need. Specific examples thereof include substances formed from cellophane, perfluorocarbon sulfonic acid (PFS)-based resin films, copolymer films of trifluorostyrene derivatives, phosphoric acid-impregnated polybenzimidazole films, aromatic polyether ketone sulfonic acid films, polystyrene sulfonic acid-polyvinyl alcohol copolymers (PSSA-PVA), polystyrene sulfonic acid-ethylene vinyl alcohol copolymers (PSSA-EVOH), and ion exchange resins having a fluorine-containing carbon sulfonic acid group (Nafion (trade name, DuPont, USA)), and the like.

In the case where an electrolyte containing a buffer substance (buffer solution) is used as the proton conductor, in order that a sufficient buffering action can be obtained, a shift of pH from an optimum pH can be sufficiently reduced, and the capacity intrinsic to the enzyme can be satisfactorily exerted even when protons are increased or decreased inside the electrode or in an enzyme-immobilized film by an enzymatic reaction through protons during a high-output operation, it is effective to specify the concentration of the buffer substance contained in the electrolyte to be 0.2 M or more and 2.5 M or less, preferably 0.2 M or more and 2 M or less, more preferably 0.4 M or more and 2 M or less, and further preferably 0.8 M or more and 1.2 M or less. In general, any buffer substance may be used as long as the substance has a $pK_a$ of 5 or more and 9 or less. Specific examples thereof include dihydrogen phosphate ion ($H_2PO_4^-$), 2-amino-2-hydroxymethyl-1,3-propanediol (abbreviated as Tris), 2-(N-morpholino)ethanesulfonic acid (MES), cacodylic acid, carbonic acid ($H_2CO_3$), hydrogen citrate ion, N-(2-acetamide)iminodiacetic acid (ADA), piperazine-N,N'-bis(2-ethanesulfonic acid) (PIPES), N-(2-acetamido)-2-aminoethanesulfonic acid (ACES), 3-(N-morpholino)propanesulfonic acid (MOPS), N-2-hydroxyethylpiperazine-N'-2-ethanesulfonic acid (HEPES), N-2-hydroxyethylpiperazine-N'-3-propanesulfonic acid (HEPPS), N-[tris(hydroxymethyl)methyl]glycine (abbreviated as tricine), glycylglycine, and N,N-bis(2-hydroxyethyl)glycine (abbreviated as bicine). Examples of a substance that produces dihydrogen phosphate ion ($H_2PO_4^-$) include sodium dihydrogenphosphate ($NaH_2PO_4$) and potassium dihydrogenphosphate ($KH_2PO_4$). As for the buffer substance, compounds having an imidazole ring are also preferable. Specific examples of the compounds having an imidazole ring include imidazole, triazole, pyridine derivatives, bipyridine derivatives, and imidazole derivatives (histidine, 1-methylimidazole, 2-methylimidazole, 4-methylimidazole, 2-ethylimidazole, ethyl imidazole-2-carboxylate, imidazole-2-carboxaldehyde, imidazole-4-carboxylic acid, imidazole-4,5-dicarboxylic acid, imidazol-1-yl-acetic acid, 2-acetylbenzimidazole, 1-acetylimidazole, N-acetylimidazole, 2-aminobenzimidazole, N-(3-aminopropyl)imidazole, 5-amino-2-(trifluoromethyl)benzimidazole, 4-azabenzimidazole, 4-aza-2-mercaptobenzimidazole, benzimidazole, 1-benzylimidazole, and 1-butylimidazole. As for the buffer substance, 2-aminoethanol, triethanolamine, N-tris(hydroxymethyl)methyl-2-aminoethanesulfonic acid (TES), N,N-bis(2-hydroxyethyl)-2-aminoethanesulfonic acid (BES), or the like may also be used. Preferably, the pH of the electrolyte containing the buffer substance is about 7, but may be any value of 1 to 14 in general. According to need, these buffer substances may also be immobilized on a film on which the enzyme and the electron mediator are immobilized.

The entire structure of this fuel cell is selected according to need. For example, when the fuel cell has a coin-type or button-type structure, preferably, the fuel cell has a structure in which the cathode, the electrolyte, and the anode are accommodated inside a space formed between a cathode current collector having a structure through which an oxidizing agent can permeate and an anode current collector having a structure through which a fuel can permeate. In this case, typically, the edge of one of the cathode current collector and the anode current collector is caulked to the other of the cathode current collector or the anode current collector, with an insulating sealing member therebetween, thereby forming the space for accommodating the cathode, the electrolyte, and the anode. However, the space is not limited to this, and the space may be formed by another processing method according to need. The cathode current collector and the anode current corrector are electrically insulated from each other through the insulating sealing member. As the insulating sealing member, typically, a gasket composed of an elastic material such as silicone rubber is used, but the insulating sealing member is not limited to this. The planar shape of the cathode current collector and the anode current corrector may be selected according to need, and is, for example, a circular shape, an elliptical shape, a quadrangular shape, a hexagonal shape, or the like. Typically, the cathode current collector has one or a plurality of oxidizing agent supply ports and the anode current collector has one or a plurality of fuel supply ports, but the configuration is not limited to this. For example, a material through which an oxidizing agent is permeable may be used as the material for the cathode current collector instead of forming the oxidizing agent supply ports. Similarly, a material through which a fuel is permeable may be used as the material for the anode current collector instead of forming the fuel supply ports. The anode current collector typically includes a fuel storage portion. This fuel storage portion may be provided integrally with the anode current collector or so as to be detached from the anode current collector. The fuel storage portion typically has a cover for sealing. In this case, a fuel may be injected into the fuel storage portion by removing the cover. The fuel may be injected from, for example, a side face of the fuel storage portion without using such a cover for sealing. When the fuel storage portion is provided so as to be detached from the anode current collector, for example, a fuel tank or fuel cartridge filled with a fuel in advance may be attached as the fuel storage portion. The fuel tank or the fuel cartridge may be disposable but is preferably a fuel tank or cartridge in which a fuel can be charged from the standpoint of effective utilization of resources. Alternatively, a used fuel tank or fuel cartridge may be exchanged for a fuel tank or fuel cartridge filled with the fuel. Furthermore, for example, the fuel storage portion may be provided in the form of a sealed container having a fuel supply port and a fuel discharge port so that the fuel is continuously supplied to the sealed container from the outside through this supply port, whereby the fuel cell can be continuously used. Alternatively, the fuel cell may be used in a state in which the fuel cell floats on the fuel contained in an open fuel tank so that the anode is located on the lower side and the cathode is located on the upper side without providing such a fuel storage portion.

This fuel cell may have a structure in which the anode, the electrolyte, the cathode, and the cathode current collector having a structure through which an oxidizing agent can permeate are sequentially provided around a predetermined central axis, and the anode current collector having a structure through which the fuel can permeate is provided so as to be electrically connected to the anode. In this fuel cell, the anode may have a cylindrical shape having a circular, elliptical, or polygonal cross-sectional shape or a columnar shape having a circular, elliptical, or polygonal cross-sectional shape. When the anode has a cylindrical shape, the anode current collector may be provided on the inner peripheral surface side of the anode, provided between the anode and the electrolyte, provided on at least one end face of the anode, or further provided at two positions or more of these, for example. In addition, the anode may be configured to store the fuel. For example, the anode may be composed of a porous material so that this anode also functions as a fuel storage portion. Alternatively, a columnar fuel storage portion may be provided on a predetermined central axis. For example, when the anode current collector is provided on the inner peripheral surface side of the anode, the fuel storage portion may be the space surrounded by the anode current collector or a container such as a fuel tank or fuel cartridge provided in the space separately from the anode current collector. This container may be detachable or fixed. The fuel storage portion has, for example, a circular columnar shape, an elliptical columnar shape, a polygonal columnar shape such as a quadrangular or hexagonal columnar shape, or the like, but the shape is not limited thereto. The electrolyte may be formed as a bag-like container so as to wrap the entire anode and anode current collector. In this case, when the fuel storage portion is fully charged with a fuel, the fuel can be brought into contact with the whole anode. In the container, at least a portion sandwiched between the cathode and the anode may be formed of an electrolyte, and other portions may be formed of a material different from the electrolyte. This container may be a sealed container having a supply port and a discharge port of a fuel so that the fuel is continuously supplied from the outside to the container through the supply port, whereby the fuel cell can be continuously used. The anode preferably has a high porosity, for example, a porosity of 60% or more so that the anode can sufficiently store the fuel therein.

A pellet electrode may be used as each of the cathode and the anode. The pellet electrode can be formed as follows. For example, a carbon-based material (particularly preferably a fine powder carbon material having high electrical conductivity and high surface area), specifically, for example, Ketjenblack (KB) imparted with high electrical conductivity or a functional carbon material such as carbon nanotube, fullerene, or the like, a binder, e.g., polyvinylidene fluoride, as required, the enzyme powder (or enzyme solution), the coenzyme powder (or coenzyme solution), the electron mediator powder (or electron mediator solution), the immobilization polymer powder (or polymer solution), and the like are mixed in an agate mortar or the like, appropriately dried, and then pressed into a predetermined shape. The thickness of the pellet electrode (electrode thickness) is also determined according to need, but is, for example, about 50 µm. For example, when a coin-type fuel cell is manufactured, a pellet electrode can be formed by pressing the above-described material for forming the pellet electrode into a circular shape (the diameter of which is, for example, 15 mm, but is not limited to this and determined according to need) using a tablet machine. When the pellet electrode is formed, the electrode thickness is adjusted to a desired value by controlling the amount of carbon contained in the material for forming the pellet electrode, the pressing pressure, and the like. When the cathode or the anode is inserted into a coin-type cell can, electrical contact is preferably established by, for example, inserting a metal mesh spacer between the cathode or the anode and the cell can.

Instead of the above-described method for manufacturing a pellet electrode, for example, a mixed solution (an aqueous or organic solvent mixed solution) of a carbon-based material, a binder, if necessary, and enzyme immobilization components (an enzyme, coenzyme, electron mediator, polymer, and the like) may be appropriately applied onto a current collector or the like and dried, and the whole may be pressed and then cut into a desired electrode size.

This fuel cell can be used for almost all things that require electric power regardless of the size. For example, the fuel cell can be used for electronic devices, mobile units (such as automobiles, two-wheeled vehicles, aircraft, rockets, and spacecraft), power units, construction machines, machine tools, power generation systems, cogeneration systems, and the like, and the output, the size, the shape, the type of fuel, and the like are determined in accordance with the use and the like.

The electronic device may be basically any type of device, and includes both portable-type devices and stationary-type devices. Specific examples thereof include cellular phones, mobile apparatuses, robots, personal computers, game machines, car-mounted apparatuses, household electric appliances, and industrial products.

In the second invention, the features described in association with the first invention are realized.

In the present invention configured as described above, since the volume of water contained in the cathode is 70% or less of the volume of pores of the cathode, a very high catalytic current value can be achieved in the cathode.

Additional features and advantages of the present invention are described in, and will be apparent from, the following Detailed Description and the Figures.

BRIEF DESCRIPTION OF THE FIGURES

FIG. 16 includes schematic views showing a specific example of the configuration of the biofuel cell according to the first embodiment of the present invention.

FIG. 22 includes a top view, a cross-sectional view, and a rear surface view that show a biofuel cell according to a third embodiment of the present invention.

FIG. 27 is a schematic view illustrating a third example of a method for use of the biofuel cell according to the third embodiment of the present invention.

FIG. 28 is a schematic view showing a biofuel cell according to a fourth embodiment of the present invention and a method for use of the biofuel cell.

DETAILED DESCRIPTION

Embodiments of the present invention will now be described with reference to the drawings.

Figure 1:
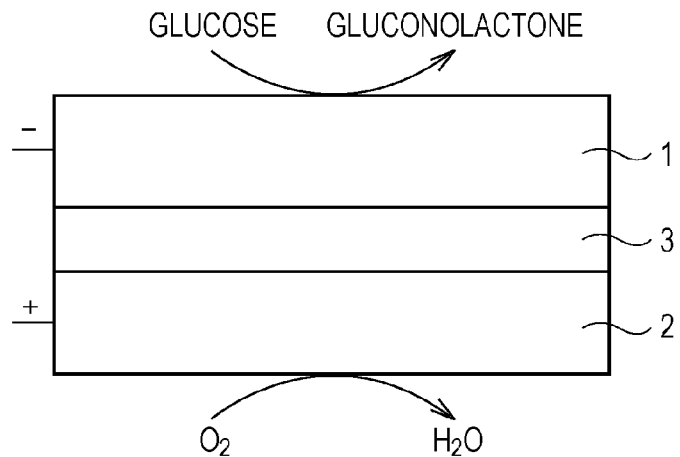
FIG. 1 is a schematic diagram showing a biofuel cell according to a first embodiment of the present invention.
Figure 2:
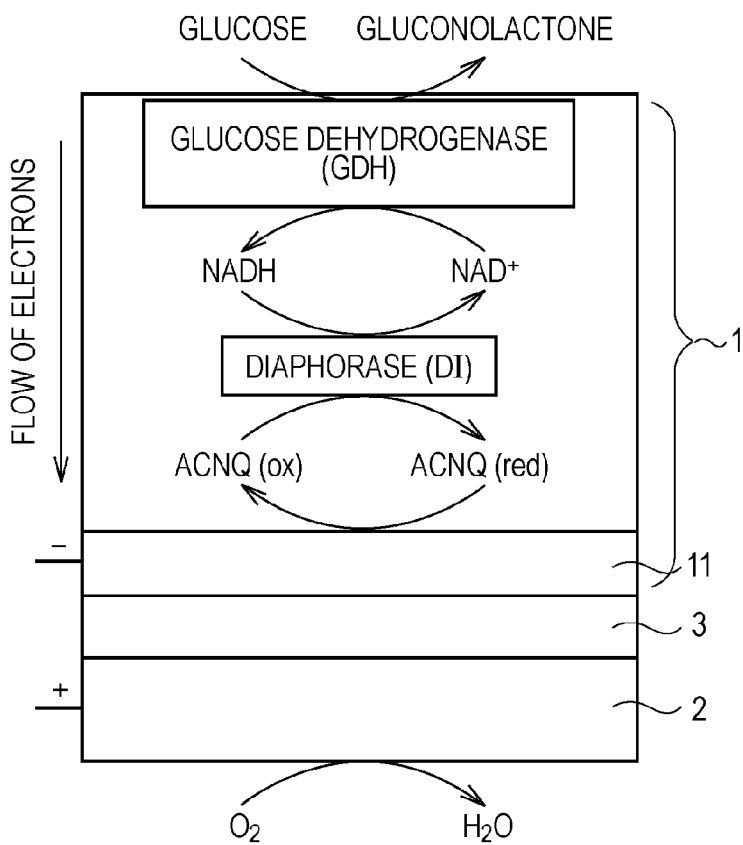
FIG. 2 is a schematic diagram that schematically shows a detailed configuration of an anode of the biofuel cell according to the first embodiment of the present invention, an example of an enzyme group immobilized on the anode, and reactions of receiving and transferring electrons caused by the enzyme group.

FIG. 1 schematically shows a biofuel cell according to a first embodiment of the present invention. In this biofuel cell, glucose is used as a fuel. FIG. 2 schematically shows a detailed configuration of an anode of the biofuel cell, an example of an enzyme group immobilized on the anode, and reactions of receiving and transferring electrons caused by the enzyme group.

As shown in FIG. 1, this biofuel cell has a structure in which an anode 1 and a cathode 2 face each other with an electrolyte layer 3 that conducts only protons therebetween. The anode 1 decomposes glucose supplied as a fuel with an enzyme to extract electrons and to generate protons ($H^+$). The cathode 2 produces water from the protons transported from the anode 1 through the electrolyte layer 3, electrons sent from the anode 1 through an external circuit, and oxygen in air, for example.

The anode 1 is constituted by immobilizing, on an electrode 11 (refer to FIG. 2) composed of, for example, porous carbon, the enzyme involved in decomposition of glucose, a coenzyme (for example, $NAD^+$, $NADP^+$, or the like), a reduced form of which is produced along with an oxidation reaction in a decomposition process of glucose, a coenzyme oxidase (for example, diaphorase) which oxidizes the reduced form of the coenzyme (for example, NADH, NADPH, or the like), and an electron mediator which receives electrons produced along with oxidation of the coenzyme from the coenzyme oxidase and transfers the electrons to the electrode 11, with an immobilizing material composed of a polymer, for example.

As the enzyme involved in the decomposition of glucose, for example, glucose dehydrogenase (GDH) can be used. The presence of this oxidase can oxidize, for example, β-D-glucose to D-glucono-δ-lactone.

Furthermore, D-glucono-δ-lactone can be decomposed to 2-keto-6-phospho-D-gluconate in the presence of two enzymes, gluconokinase and phosphogluconate dehydrogenase (PhGDH). That is, D-glucono-δ-lactone is converted into D-gluconate by hydrolysis. D-gluconate is phosphorylated by hydrolysis of adenosine triphosphate (ATP) to adenosine diphosphate (ADP) and phosphoric acid in the presence of gluconokinase to be converted into 6-phospho-D-gluconate. The resulting 6-phospho-D-gluconate is oxidized to 2-keto-6-phospho-D-gluconate by the action of the oxidase PhGDH.

Furthermore, glucose can also be decomposed to $CO_2$ through the use of glycometabolism besides the above-described decomposition process. This decomposition process through the use of glycometabolism is broadly classified into decomposition of glucose and production of pyruvic acid through a glycolytic pathway and a TCA cycle. These are well-known reaction systems.

The oxidation reaction in the decomposition process of monosaccharides is conducted with a reduction reaction of a coenzyme. This coenzyme is almost determined depending on the enzyme that acts. In the case of GDH, $NAD^+$ is used as the coenzyme. That is, when β-D-glucose is oxidized to D-glucono-δ-lactone by the action of GDH, $NAD^+$ is reduced to NADH and to generate $H^+$.

The produced NADH is immediately oxidized to $NAD^+$ in the presence of diaphorase (DI), and two electrons and two $H^+$ are generated. Accordingly, two electrons and two $H^+$ per molecule of glucose are produced in a one-stage oxidation reaction. Four electrons and four $H^+$ in total are produced in a two-stage oxidation reaction.

The electrons generated in the above process are transferred from diaphorase to the electrode 11 through the electron mediator, and $H^+$ are transferred to the cathode 2 through the electrolyte layer 3.

The electron mediator receives and transfers electrons from and to the electrode 11, and the output voltage of the fuel cell depends on the oxidation-reduction potential of the electron mediator. That is, in order to achieve a higher output voltage, an electron mediator having a more negative electric potential may be selected for the anode 1 side. However, the reaction affinity of the electron mediator to the enzyme, the electron-exchange rate with the electrode 11, the structural stability to inhibiting factors (such as light and oxygen), and the like must also be considered. From these standpoints, 2-amino-3-carboxy-1,4-naphthoquinone (ACNQ), vitamin K3, or the like is preferable as the electron mediator that acts on the anode 1. Examples of other usable electron mediators include compounds having a quinone skeleton; metal complexes of osmium (Os), ruthenium (Ru), iron (Fe), cobalt (Co), or the like; viologen compounds such as benzyl viologen; compounds having a nicotinamide structure; compounds having a riboflavin structure; and compounds having a nucleotide phosphate structure.

The electrolyte layer 3 is a proton conductor that transports $H^+$ generated in the anode 1 to the cathode 2 and is constituted by a material that does not has electron conductivity and that can transport $H^+$. This electrolyte layer 3 may be composed of a material that is adequately selected from materials mentioned above, for example. In such a case, the electrolyte layer 3 includes one that contains a buffer solution containing a compound having an imidazole ring as a buffer substance. The compound having an imidazole ring can be adequately selected from compounds described above, for example, imidazole. The concentration of the compound having an imidazole ring, which serves as a buffer substance, is selected according to need, and the compound is preferably incorporated in a concentration of 0.2 M or more and 3 M or less. In such a case, a high buffering capacity can be achieved and the capacity intrinsic to the enzyme can be satisfactorily exerted even when the fuel cell is operated at a high output. Furthermore, a too large or too small ionic strength (I.S.) adversely affects the enzyme activity. In consideration of also the electrochemical responsiveness, an appropriate ionic strength, for example, about 0.3 is preferable. However, as for the pH and the ionic strength, optimum values are different depending on the enzymes used, and are not limited to the above values.

The enzyme, the coenzyme, and the electron mediator are preferably immobilized on the electrode 11 using an immobilizing material so that a phenomenon of an enzymatic reaction occurring in the vicinity of the electrode can be efficiently detected as an electrical signal. Furthermore, by immobilizing also the enzyme that decomposes a fuel and the coenzyme on the electrode 11, the enzymatic reaction system of the anode 1 can be stabilized. Examples of the immobilizing material include a combination of glutaraldehyde (GA) and poly-L-lysine (PLL) and a combination of sodium polyacrylate (PAAcNa) and poly-L-lysine (PLL). These may be used alone or another polymer may be further used. When the combination of glutaraldehyde and poly-L-lysine is used as the immobilizing material, the enzyme immobilizing ability possessed by these individual substances can be markedly improved, thereby achieving an excellent enzyme immobilizing ability of the immobilizing material as a whole. In this case, the optimum value of the composition ratio between glutaraldehyde and poly-L-lysine varies depending on the enzyme to be immobilized and a substrate of the enzyme, but may be generally a desired composition ratio. Specifically, for example, when an aqueous solution of glutaraldehyde (0.125%) and an aqueous solution of poly-L-lysine (1%) are used, the ratio may be, for example, 1:1, 1:2, or 2:1.

FIG. 2 shows, as an example, a case where an enzyme involved in decomposition of glucose is glucose dehydrogenase (GDH), a coenzyme, a reduced form of which is produced along with an oxidation reaction in the decomposition process of glucose is $NAD^+$, a coenzyme oxidase that oxidizes NADH, which is the reduced form of the coenzyme, is diaphorase (DI), and an electron mediator that receives, from the coenzyme oxidase, electrons produced along with oxidation of the coenzyme and transfers the electrons to the electrode 11 is ACNQ.

The cathode 2 is configured so that an oxygen reductase and an electron mediator that receives and transfers electrons from and to an electrode are immobilized on the electrode composed of a material having pores, such as porous carbon. For example, bilirubin oxidase (BOD), laccase, ascorbic acid oxidase, or the like can be used the oxygen reductase. As the electron mediator, for example, hexacyanoferrate ions produced by ionization of potassium hexacyanoferrate may be used. The electron mediator is preferably immobilized at a sufficiently high concentration, for example, $0.64 \times 10^{-6}$ mol/$mm^2$ or more on average.

In the cathode 2, oxygen in air is reduced by $H^+$ transferred from the electrolyte layer 3 and electrons sent from the anode 1 in the presence of the oxygen reductase to produce water.

During the operation (during the use) of the fuel cell configured as described above, when glucose is supplied to the anode 1 side, the glucose is decomposed by a catabolic enzyme containing an oxidase. As a result of the involvement of the oxidase in this decomposition process of a monosaccharide, electrons and $H^+$ can be produced at the anode 1 side and a current can be generated between the anode 1 and the cathode 2.

In this biofuel cell, from before the start of the operation (before use) to during the operation (during use), the volume of water contained in the cathode 2 is controlled to be 70% or less of the volume of pores of the cathode 2. This control of the amount of moisture can be performed by, for example, selection of the material constituting the electrolyte layer 3. For example, when cellophane is used as the electrolyte layer 3, the volume of water contained in the cathode 2 can be controlled to be about 45% of the volume of the pores of the cathode 2. Well-known techniques used in direct methanol fuel cells may be employed in this control of the amount of moisture. That is, a method for controlling the amount of moisture in which a fluorine-based resin (e.g., Nafion, polyvinylidene fluoride, polytetrafluoroethylene, or the like) or the like is used as the cathode 2 or a layer that is in contact with the cathode 2 may be employed.

Figure 3:
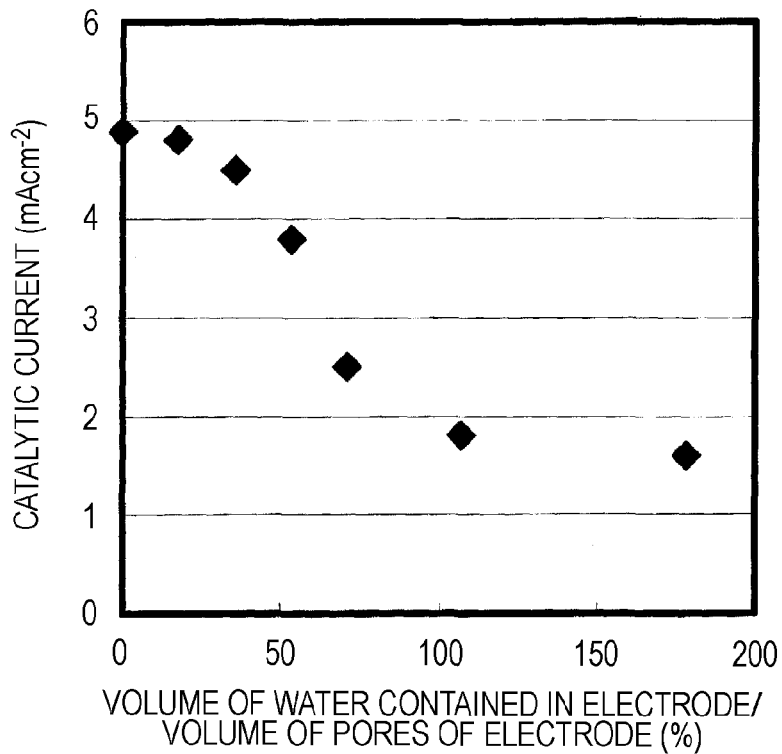
FIG. 3 is a schematic diagram showing the results of experiments conducted for measuring a change in a catalytic current value due to the amount of moisture contained in a cathode of the biofuel cell according to the first embodiment of the present invention.

Here, a description will be made of the results obtained by measuring a change in a catalytic current value due to the amount of moisture contained in the cathode 2. FIG. 3 shows the results. The horizontal axis represents (volume of water contained in electrode (cathode 2)/(volume of pores of electrode (cathode 2)) (%) and the vertical axis represents a catalytic current. This measurement was conducted in a state in which film-like cellophane was placed on the cathode 2 and an imidazole/hydrochloric acid buffer solution was in contact with the cellophane. As for the cathode 2, enzyme/electron mediator-immobilized electrodes prepared as described below were used. First, commercially available carbon felt (manufactured by TORAY Industries Inc., BO050) was used as porous carbon, and this carbon felt was cut into 1 cm squares. Next, the carbon felt was sequentially impregnated with 80 μL of hexacyanoferrate ions (100 mM), 80 μL of poly-L-lysine (1 wt %), and 80 μL of a BOD solution (50 mg/mL), and then dried to prepare the enzyme/electron mediator-immobilized electrodes. Electrodes each prepared by adding in advance 0, 5, 10, 15, 20, 30, or 50 μL of water to the above electrodes were used as working electrodes. Each of these electrodes has a thickness of 0.35 mm and an area of 1 cm square. Accordingly, the volume of each of the electrodes is 0.035 $cm^3$. The porosity of the carbon felt used in the electrodes was measured with a mercury porosimeter (Autopore IV 9500 series, manufactured by Shimadzu Corporation). According to the result, the porosity was estimated to 80%. Alternatively, a gas adsorption specific surface area measuring apparatus (manufactured by BEL Japan, Inc., BELSORP-max) or the like may be used for the measurement of the porosity. As described above, since the porosity of the carbon felt used in the electrodes is 80%, the volume of the pores of each of the electrodes is 0.028 $cm^3$. Therefore, in the case where 30 μL or 50 μL of moisture is added, it is believed that all the pores in the electrode are immersed in water, in other words, submerged in water. The amount of moisture contained in electrodes can be easily measured using a Karl Fischer moisture meter (for example, model VA-100, manufactured by Dia Instruments Co., Ltd.) or the like.

As is understood from FIG. 3, the catalytic current value changes markedly at a threshold of (volume of water contained in electrode)/(volume of pores of electrode)=70%, and very high catalytic current values are achieved at 70% or less. Looking at it another way, a high catalytic current value can be achieved in the cathode 2 by controlling the (volume of water contained in electrode)/(volume of pores of electrode) to be 70% or less. Specifically, the case where 15 μL of water is added to the electrode corresponds to (volume of water contained in electrode)/(volume of pores of electrode)=53%. The catalytic current value obtained in this case is larger than the catalytic current values in the cases where water is added to the electrode in amounts of 20, 30, and 50 μL ((volume of water contained in electrode)/(volume of pores of electrode) is 71.4%, 107%, and 179%, respectively) by as large as about 1.5 to 2.4 times. In the case where 20 μL of water is added to the electrode ((volume of water contained in electrode)/(volume of pores of electrode)=71.4%), although the pores in the electrode are not submerged in water, only a low catalytic current is obtained as in the case where pores in the electrode are submerged in water (the case where the amount of moisture added is 30 μL or 50 μL). Considering these results, this indicates that it is insufficient that the pores in the electrode are not simply submerged in water and it is necessary that a certain fraction or more of the pores in the electrode be not filled with water. A condition therefor is (volume of water contained in electrode)/(volume of pores of electrode)=70%.

Figure 4:
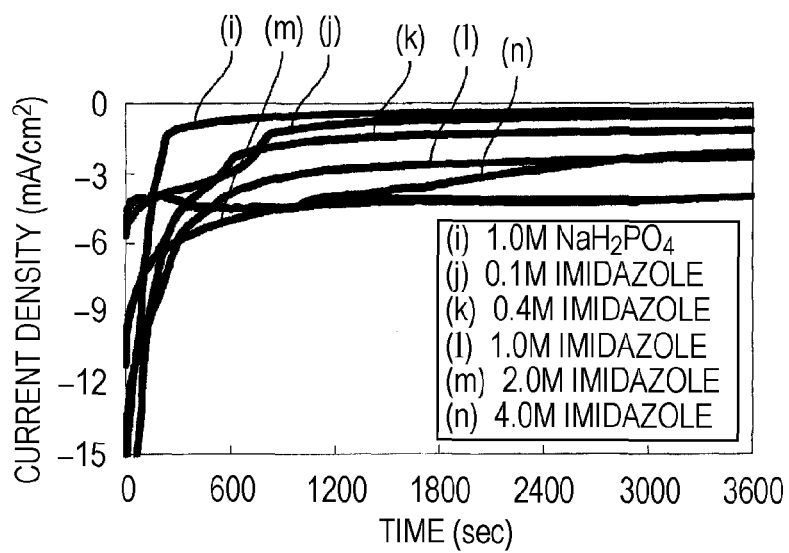
FIG. 4 is a schematic diagram showing the results of chronoamperometry conducted for evaluating the biofuel cell according to the first embodiment of the present invention.
Figure 5:
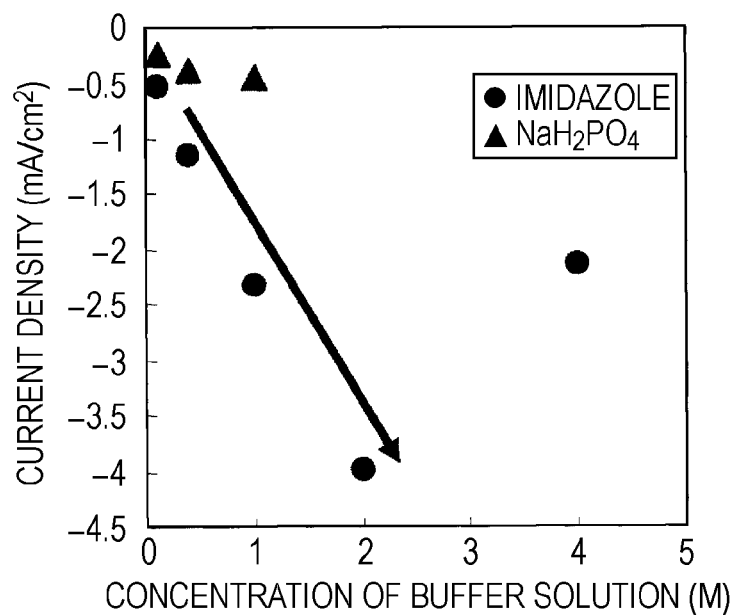
FIG. 5 is a schematic diagram showing the relationship between the concentration of a buffer solution and the resulting current density, the relationship being obtained from the results of chronoamperometry conducted for evaluating the biofuel cell according to the first embodiment of the present invention.
Figure 6:
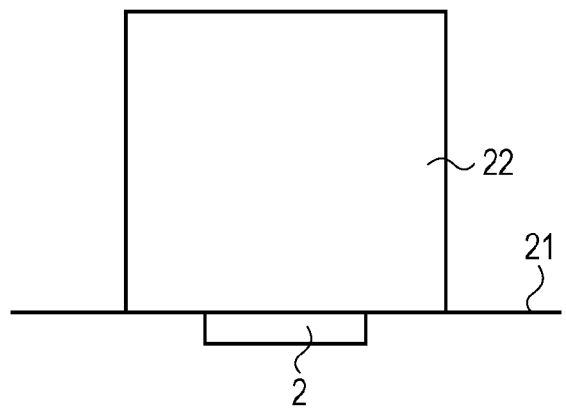
FIG. 6 is a schematic view showing a system of measurement used in the measurement of chronoamperometry shown in FIG. 4.

Next, a description will be made of an effect of maintaining and improving the current value in the case where BOD was immobilized on the cathode 2 as an oxygen reductase and a solution prepared by mixing imidazole and hydrochloric acid and adjusting the pH of the resulting mixture to be 7 was used as a buffer solution. Table 1 and FIG. 4 show the results of chronoamperometry measured when the concentration of imidazole was varied in this case. In addition, FIG. 5 shows the dependency of the current value (the value of current density after 3,600 seconds in Table 1 and FIG. 4) on the concentration of the buffer solution (the concentration of a buffer substance in a buffer solution). For comparison, Table 1 and FIG. 5 also show the results in the case where a 1.0 M $NaH_2PO_4$/NaOH buffer solution (pH 7) was used as a buffer solution. This measurement was performed in a state in which film-like cellophane 21 was placed on a cathode 2 and a buffer solution 22 was in contact with the cellophane 21, as shown in FIG. 6. Enzyme/electron mediator-immobilized electrodes prepared as described below were used as the cathode 2. First, commercially available carbon felt (manufactured by TORAY Industries Inc., BO050) was used as porous carbon, and this carbon felt was cut into 1 cm squares. Next, the carbon felt was sequentially impregnated with 80 μL of hexacyanoferrate ions (100 mM), 80 μL of poly-L-lysine (1 wt %), and 80 μL of a BOD solution (50 mg/mL), and then dried to prepare the enzyme/electron mediator-immobilized electrodes. Two enzyme/electron mediator-immobilized electrodes thus prepared were overlapped and used as the cathode 2.

TABLE 1

| | Current density (mA/$cm^2$) | | | | | |
|---|---|---|---|---|---|---|
| | 1 sec | 180 sec | 300 sec | 600 sec | 1,800 sec | 3,600 sec |
| 1.0M $NaH_2PO_4$ | −17.22 | −3.11 | −1.10 | −0.73 | −0.41 | −0.34 |
| 0.1M imidazole | −5.64 | −3.98 | −3.71 | −2.98 | −0.70 | −0.54 |
| 0.4M imidazole | −11.18 | −6.37 | −4.69 | −2.48 | −1.35 | −1.16 |
| 1.0M imidazole | −15.59 | −8.44 | −5.81 | −3.86 | −2.60 | −2.32 |
| 2.0M imidazole | −25.10 | −7.39 | −5.88 | −5.01 | −4.20 | −3.99 |
| 4.0M imidazole | −5.08 | −3.90 | −4.19 | −4.53 | −3.47 | −2.13 |

As is understood from Table 1 and FIG. 4, when the concentration of $NaH_2PO_4$ was 1.0 M, the initial current was sufficient but the current was significantly decreased after 3,600 seconds. In contrast, when the concentration of imidazole was 0.4 M, 1.0 M, and 2.0 M, a decrease in the current was hardly observed even after 3,600 seconds. As is understood from FIG. 5, the current value linearly increased in the range of 0.2 to 2.5 M of the concentration of imidazole. Furthermore, although both a $NaH_2PO_4$/NaOH buffer solution and an imidazole/hydrochloric acid buffer solution have a $pK_a$ of about 7 and substantially the same oxygen solubility, in the case where the concentrations of the buffer solutions were the same each other, a larger oxygen reduction current was obtained in the buffer solution containing imidazole.

Figure 7:
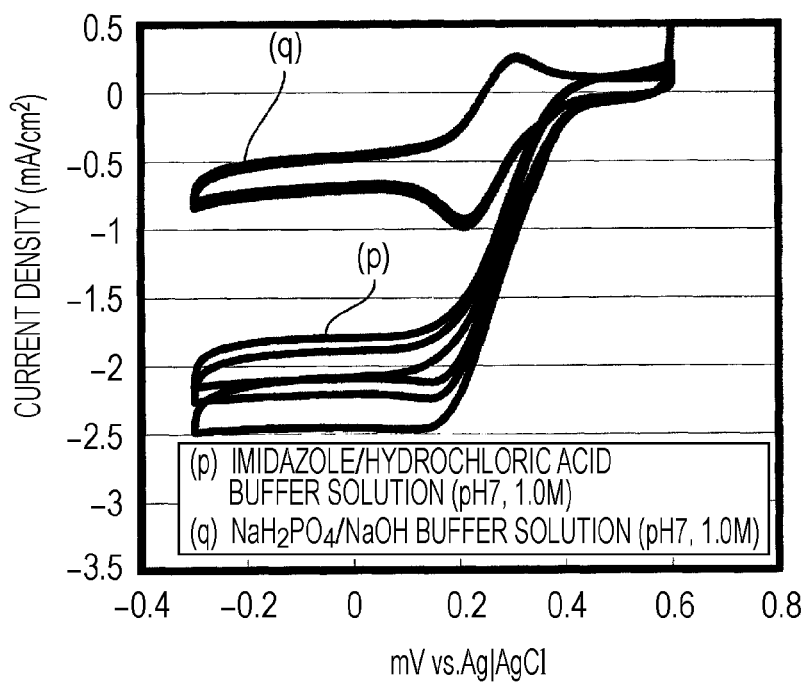
FIG. 7 is a schematic diagram showing the results of cyclic voltammetry conducted for evaluating the biofuel cell according to the first embodiment of the present invention.
Figure 8:
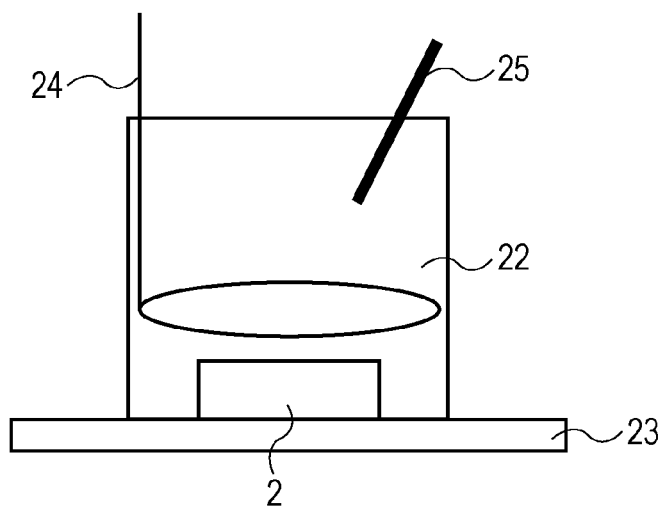
FIG. 8 is a schematic view showing a system of measurement used in the measurement of cyclic voltammetry shown in FIG. 7.

After chronoamperometry was performed for 3,600 seconds as described above, cyclic voltammetry (CV) was performed in an electric potential range of −0.3 to +0.6 V. The results are shown in FIG. 7. Note that this measurement was performed in a state in which, as shown in FIG. 8, a cathode 2 composed of the same enzyme/electron mediator-immobilized electrode as described above was used as a working electrode, this working electrode was placed on an air-permeable polytetrafluoroethylene (PTFE) membrane 23, and a buffer solution 22 was in contact with the cathode 2. A counter electrode 24 and a reference electrode 25 were immersed in the buffer solution 22, and an electrochemical measuring device (not shown) was connected to the cathode 2, which served as a working electrode, the counter electrode 24, and the reference electrode 25. A Pt wire was used as the counter electrode 24, and a Ag|AgCl was used as the reference electrode 25. The measurement was performed at the atmospheric pressure, and the measurement temperature was 25° C. Two types of buffer solution, i.e., an imidazole/hydrochloric acid buffer solution (pH 7, 1.0 M) and a $NaH_2PO_4$/NaOH buffer solution (pH 7, 1.0 M) were used as the buffer solution 22.

Referring to FIG. 7, it is understood that when the imidazole/hydrochloric acid buffer solution (pH 7, 1.0 M) was used as the buffer solution 22, very satisfactory CV characteristics were achieved.

From the above results, it was confirmed that an advantage lies in the imidazole buffer solution even when the system of measurement was changed.

Figure 9:
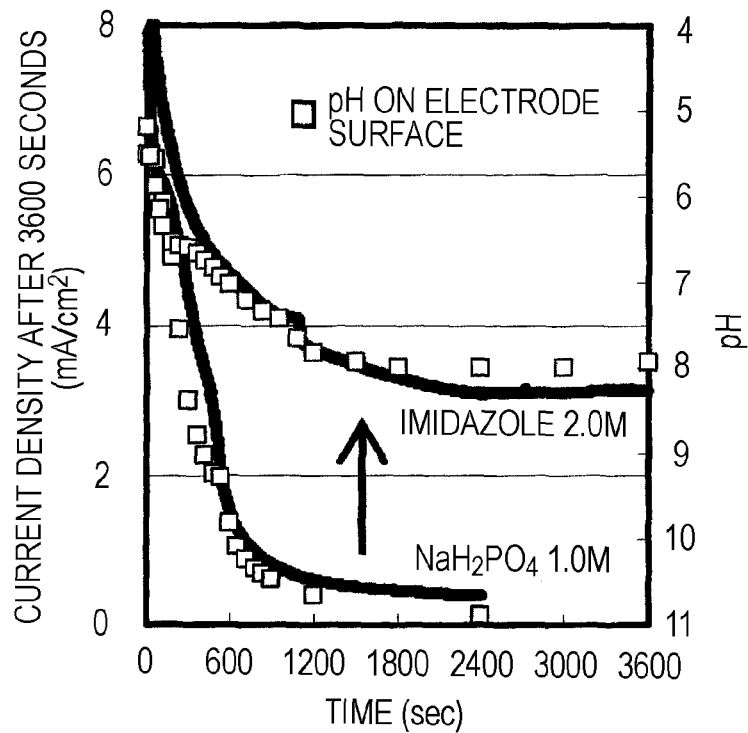
FIG. 9 is a schematic diagram showing the results of chronoamperometry conducted in the biofuel cell according to the first embodiment of the present invention using a buffer solution containing imidazole and a $NaH_2PO_4$ buffer solution.

FIG. 9 shows the results of chronoamperometry performed by the same method as described above in which BOD was immobilized in the cathode 2 and a 2.0 M imidazole/hydrochloric acid buffer solution and a 1.0 M $NaH_2PO_4$/NaOH buffer solution were used, and the measurement results of the pH on the electrode surface obtained during the chronoamperometry. Here, pKa of the imidazole/hydrochloric acid buffer solution is 6.95, the electrical conductivity is 52.4 mS/cm, the oxygen solubility is 0.25 mM, and the pH is 7. In addition, pKa of the $NaH_2PO_4$/NaOH buffer solution is 6.82 ($H_2PO_4^-$), the electrical conductivity is 51.2 mS/cm, the oxygen solubility is 0.25 mM, and the pH is 7. As is understood from FIG. 9, in the case where the 2.0 M imidazole/hydrochloric acid buffer solution was used, a high current density about 15 times higher than that in the case where the 1.0 M $NaH_2PO^4$/NaOH buffer solution was used was achieved. Furthermore, referring to FIG. 9, it is found that the change in the current substantially corresponds to the change in the pH on the electrode surface. The reasons why these results were obtained will be described with reference to FIGS. 10 and 11.

Figure 10:
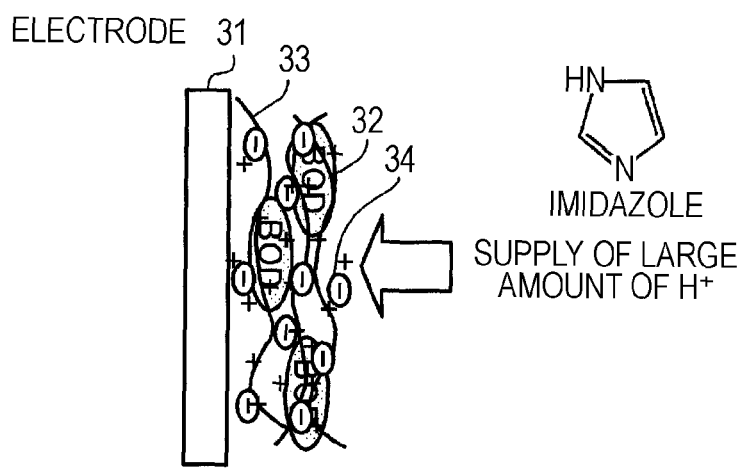
FIG. 10 is a schematic view for explaining a mechanism that a large current can be constantly obtained in the case where the buffer solution containing imidazole is used in the biofuel cell according to the first embodiment of the present invention.
Figure 11:
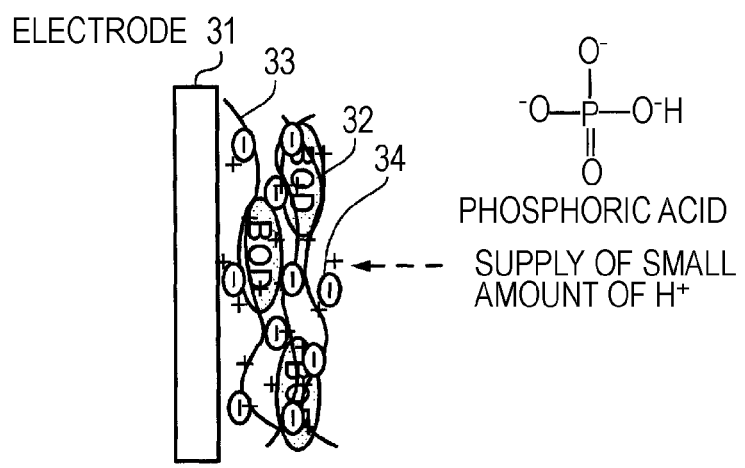
FIG. 11 is a schematic view for explaining a mechanism that the current is decreased in the case where the $NaH_2PO_4$ buffer solution is used in the biofuel cell according to the first embodiment of the present invention.

FIGS. 10 and 11 each show a state where BOD 32 is immobilized on an electrode 31 together with an electron mediator 34 using an immobilizing material 33 such as a polyion complex. As shown in FIG. 10, it is believed that when the 2.0 M imidazole/hydrochloric acid buffer solution is used, a sufficiently large amount of proton ($H^+$) is supplied, whereby a high buffering capacity is achieved to stabilize the pH, thus constantly obtaining a high current density. In contrast, as shown in FIG. 11, it is believed that when the 1.0 M $NaH_2PO_4$/NaOH buffer solution is used, the amount of $H^+$ being supplied is small, resulting in an insufficient buffering capacity, and thus the pH is significantly increased thereby decreasing the current density.

Figure 12:
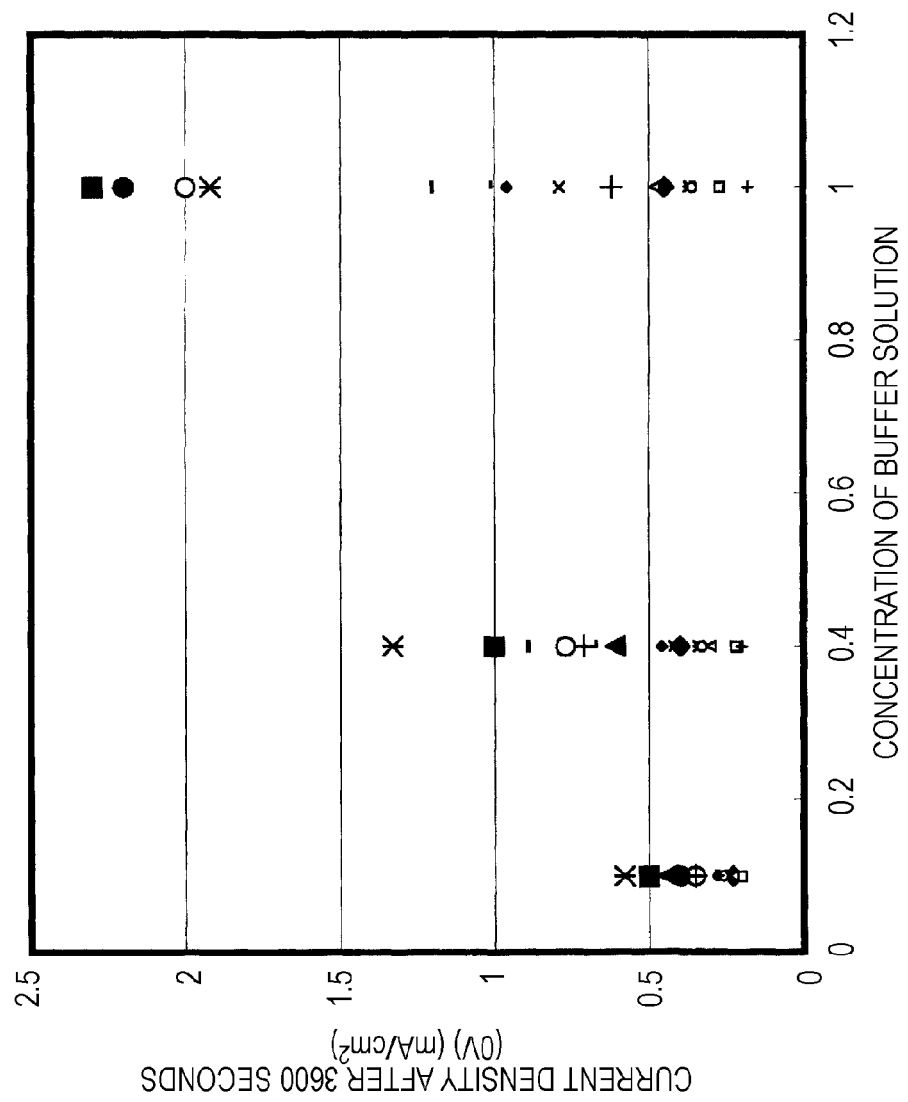
FIG. 12 is a schematic diagram showing the relationship between the concentration of a buffer solution and the current density in the case where various buffer solutions were used in the biofuel cell according to the first embodiment of the present invention.
Figure 13:
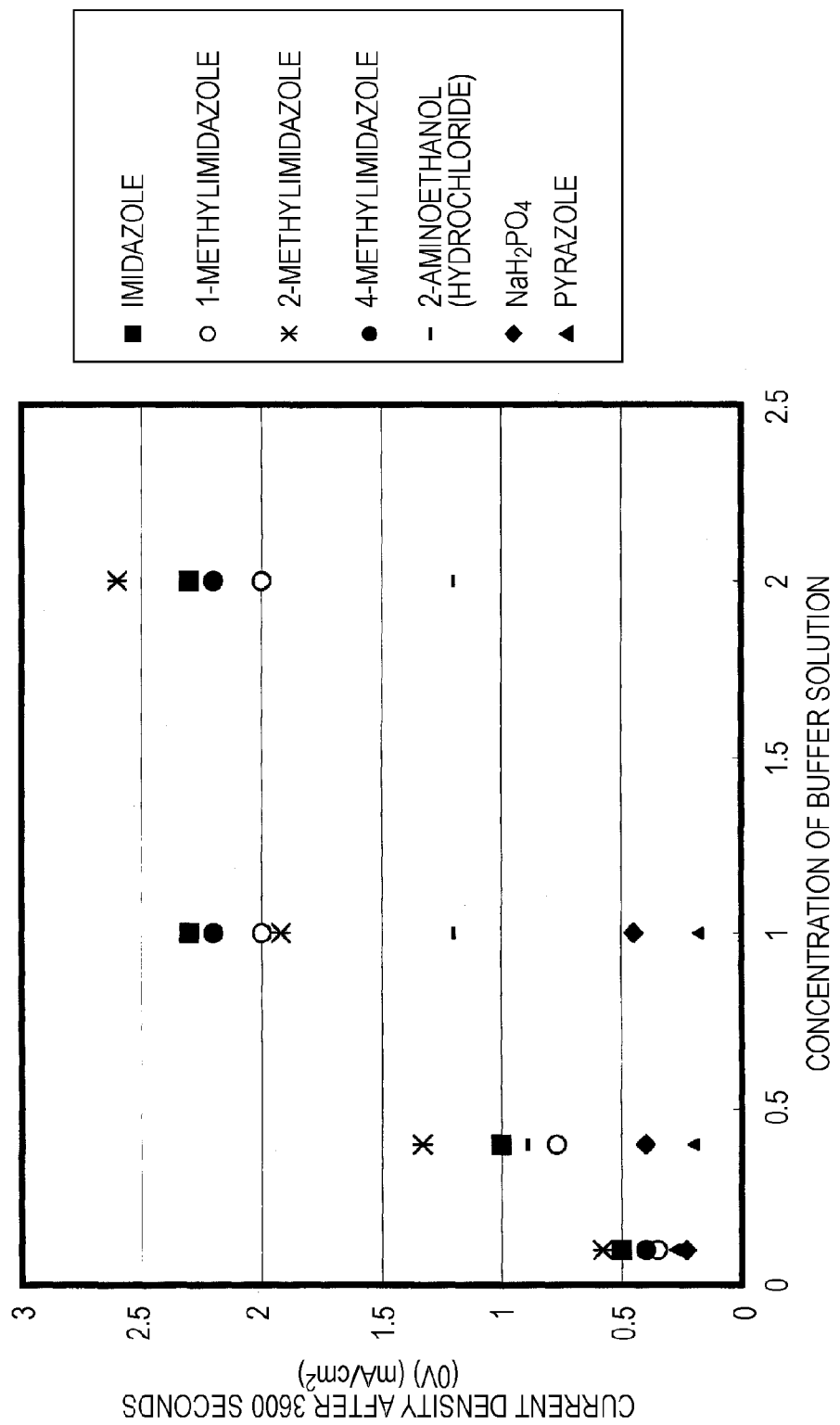
FIG. 13 is a schematic diagram showing the relationship between the concentration of a buffer solution and the current density in the case where various buffer solutions were used in the biofuel cell according to the first embodiment of the present invention.

FIGS. 12 and 13 each show a change in the current density after 3,600 seconds (one hour) to the concentration of a buffer solution when various buffer solutions were used. As is understood from FIGS. 12 and 13, in the cases where buffer solutions containing a compound having an imidazole ring are used, high current densities are obtained as a whole, as compared with the cases where other buffer solutions such as a buffer solution containing $NaH_2PO_4$ are used, and this tendency becomes particularly significant as the concentration of the buffer solution increases. Furthermore, referring to FIGS. 12 and 13, it is found that, also in the cases where 2-aminoethanol, triethanolamine, and a buffer solution containing TES or BES are used as a buffer substance, high current densities are obtained, and this tendency becomes particularly significant as the concentration of the buffer solution increases.

Figure 14:
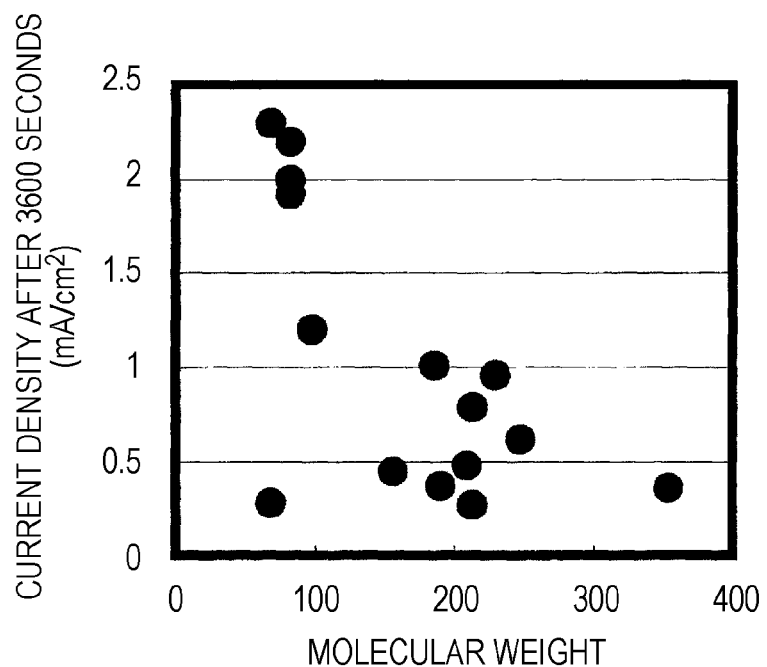
FIG. 14 is a schematic diagram showing the relationship between the molecular weight of a buffer substance of a buffer solution and the current density in the case where various buffer solutions were used in the biofuel cell according to the first embodiment of the present invention.
Figure 15:
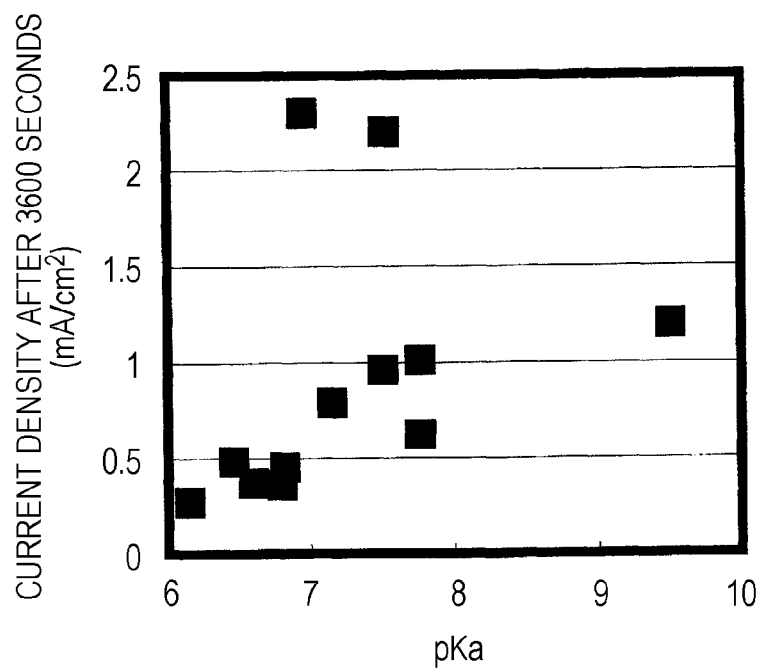
FIG. 15 is a schematic diagram showing the relationship between $pK_a$ of a buffer solution and the current density in the case where various buffer solutions were used in the biofuel cell according to the first embodiment of the present invention.

FIGS. 14 and 15 are plots of the current density after 3,600 seconds to the molecular weight of a buffer substance and $pK_a$, respectively, when the buffer solutions shown in FIGS. 12 and 13 were used.

FIGS. 16(A) and 16(B) show a specific example of the configuration of this biofuel cell.

As shown in FIGS. 16(A) and 16(B), this biofuel cell has a structure in which an anode 1 composed of an enzyme/electron mediator-immobilized carbon electrode prepared by immobilizing the above-described enzyme and electron mediator on carbon felt of 1 $cm^2$ with an immobilizing material and a cathode 2 composed of an enzyme/electron mediator-immobilized carbon electrode prepared by immobilizing the above-described enzyme and electron mediator on carbon felt of 1 $cm^2$ with an immobilizing material face each other, with an electrolyte layer 3 containing, as a buffer substance, a compound having an imidazole ring or 2-aminoethanol hydrochloride therebetween. In this case, Ti current collectors 41 and 42 are respectively provided under the cathode 2 and on the anode 1 so that current collection can be easily performed. Symbols 43 and 44 denote clamping plates. These clamping plates 43 and 44 are fastened together with screws 45, and the whole of the cathode 2, the anode 1, the electrolyte layer 3, and the Ti current collectors 41 and 42 are sandwiched therebetween. A circular recess 43a for air intake is provided on one surface (outside surface) of the clamping plate 43. A large number of holes 43b penetrating to the other surface are provided in the bottom face of the recess 43a. These holes 43b serve as air supply channels to the cathode 2. On the other hand, a circular recess 44a for fuel charge is provided on one surface (outside surface) of the clamping plate 44. A large number of holes 44b penetrating to the other surface are provided in the bottom face of the recess 44a. These holes 44b serve as fuel supply channels to the anode 1. A spacer 46 is provided on the peripheral portion of the other surface of the clamping plate 44 such that when the clamping plates 43 and 44 are fastened together with the screws 45, the distance therebetween becomes a predetermined distance.

As shown in FIG. 16(B), a load 47 was connected between the Ti current collectors 41 and 42. A glucose/buffer solution was placed as a fuel in the recess 44a of the fixing plate 44, and power generation was conducted. Two types of buffer solution, i.e., a 2.0 M imidazole/hydrochloric acid buffer solution (pH 7) and a 1.0 M $NaH_2PO_4$/NaOH buffer solution (pH 7) were used as a buffer solution. The concentration of glucose was 0.4 M. The operating temperature was 25° C.

Figure 17:
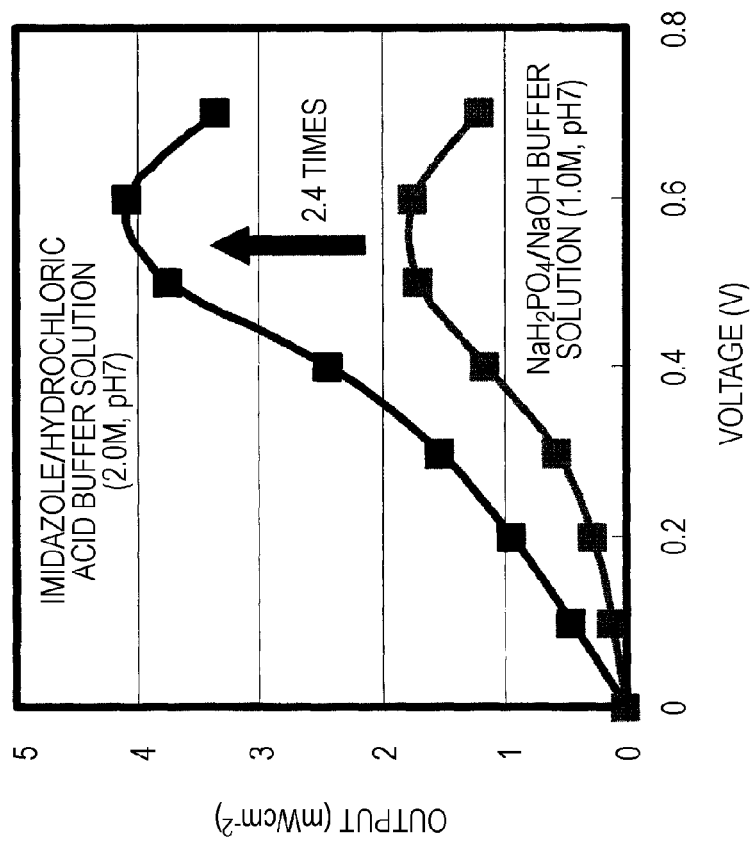
FIG. 17 is a schematic diagram showing the measurement results of the output of the biofuel cell used in the evaluation in the first embodiment of the present invention.

FIG. 17 shows the output characteristics. As shown in FIG. 17, in the case where the 2.0 M imidazole/hydrochloric acid buffer solution was used as the buffer solution, the output (electric power density) is larger than that in the case where the $NaH_2PO_4$/NaOH buffer solution was used by as large as about 2.4 times.

As described above, according to the first embodiment, before the start of the operation to during the operation, since the volume of water contained in the cathode 2 is 70% or less of the volume of pores of the cathode 2, a high catalytic current can be obtained in the cathode 2, and furthermore, a high current value can be continuously obtained in the biofuel cell. In addition, since the electrolyte layer 3 contains, as a buffer substance, a compound having an imidazole ring, a sufficient buffering capacity can be achieved. Accordingly, during high-output operation of the biofuel cell, even when an increase or a decrease in protons is caused by an enzymatic reaction via a proton inside the electrode of protons or in the enzyme-immobilized film, a sufficient buffering capacity can be achieved and a shift of the pH of the electrolyte around the enzyme from an optimum pH can be sufficiently decreased. Therefore, the capacity intrinsic to the enzyme can be satisfactorily exerted and electrode reactions caused by the enzyme, the coenzyme, electron mediator, and the like can be efficiently and constantly performed. Consequently, a high-performance biofuel cell that can be operated at a high output can be realized. This biofuel cell is suitably applied to a power supply of various electronic devices, mobile units, power generation systems, and the like.

Next, a biofuel cell according to a second embodiment of the present invention will be described.

In this biofuel cell, an electrolyte layer 3 has an electric charge having the same sign as the electric charge of an oxidized form or a reduced form of an electron mediator used in a cathode 2 and an anode 1. For example, at least a surface on the cathode 2 side of the electrolyte layer 3 is negatively charged and has a negative electric charge. Specifically, for example, a polyanion having a negative electric charge is contained in whole or a part of the portion of at least the cathode 2 side of the electrolyte layer 3. Preferably, Nafion (trade name, DuPont, USA), which is an ion-exchange resin having a fluorine-containing carbon sulfonic acid group, is used as this polyanion.

Here, a description will be made of the results of comparative experiments conducted in order to verify that when the electrolyte layer 3 has an electric charge having the same sign as the electric charge of an oxidized form or a reduced form of the electron mediator, passing of the oxidized form or the reduced form of the electron mediator through the electrolyte layer 3 can be prevented.

Figure 18:
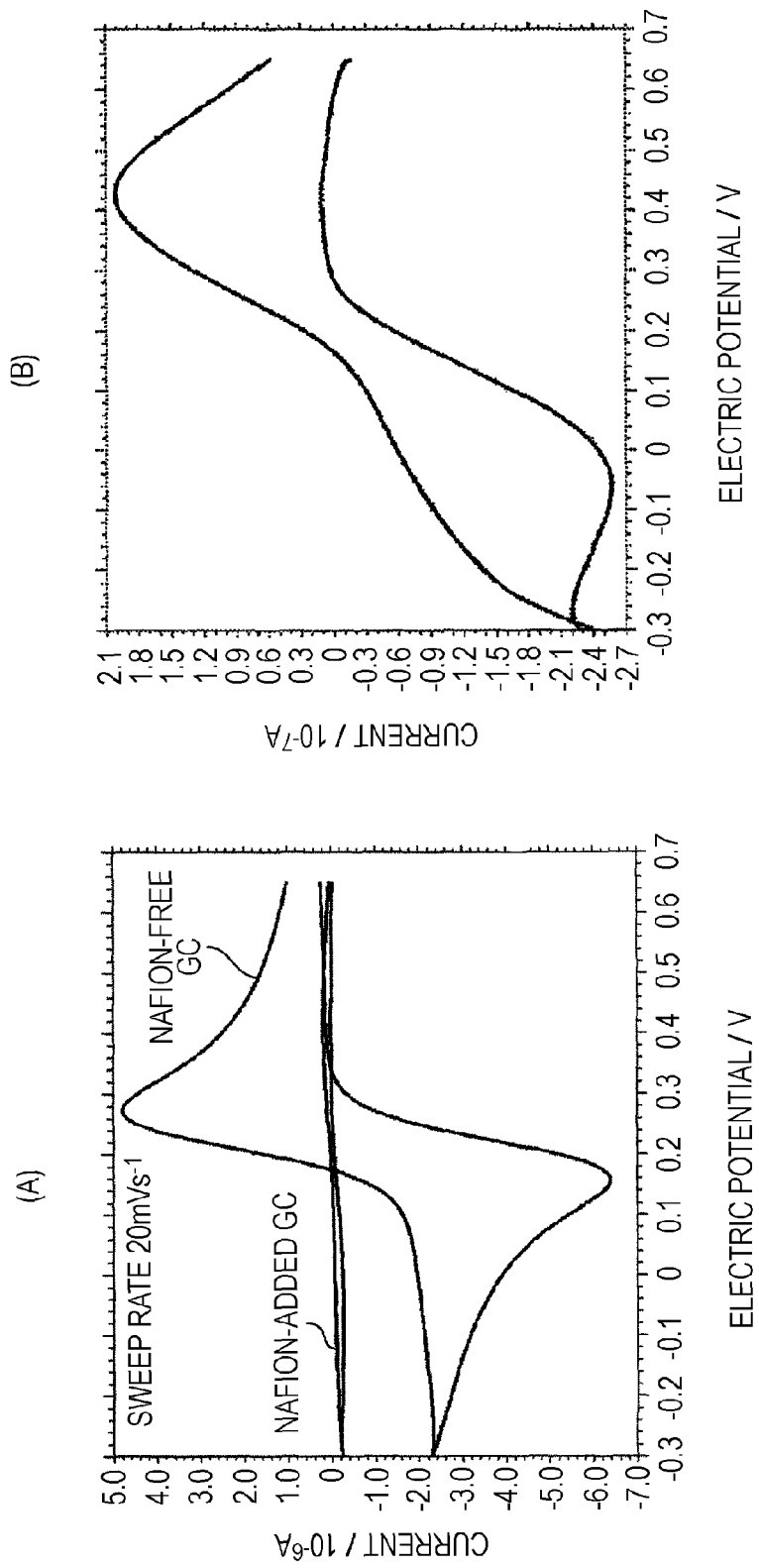
FIG. 18 includes schematic diagrams showing the results of cyclic voltammetry conducted for verifying a permeation-preventing effect of an electron mediator in a biofuel cell according to a second embodiment of the present invention.

First, two commercially available glassy carbon (GC) electrodes (diameter: 3 mm) were prepared, and both electrodes were polished and washed. Next, 5 μL of an emulsion (20%) of commercially available Nafion, which is a polyanion, was added to one of the glassy carbon electrode, and the electrode was dried. Next, the two glassy carbon electrodes were immersed in a 1 mM aqueous hexacyanoferrate ion (polyvalent anion) solution (50 mM $NaH_2PO_4$/NaOH buffer solution, pH 7), and cyclic voltammetry (CV) was performed at a sweep rate of 20 mVs$^{-1}$. The results are shown in FIG. 18(A). FIG. 18(B) shows enlarged CV curves in the case where the Nafion-added glassy carbon electrode was used in FIG. 18(A). As is understood from FIGS. 18(A) and 18(B), in the Nafion-added glassy carbon electrode, an oxidation-reduction peak current due to the hexacyanoferrate ions serving as an electron mediator was 1/20 or less, as compared with the glassy carbon electrode to which Nafion was not added. This result shows that the hexacyanoferrate ions, which are polyvalent anions having a negative electric charge as in this Nafion, do not diffuse or pass through the Nafion, which is a polyanion having a negative electric charge.

Figure 19:
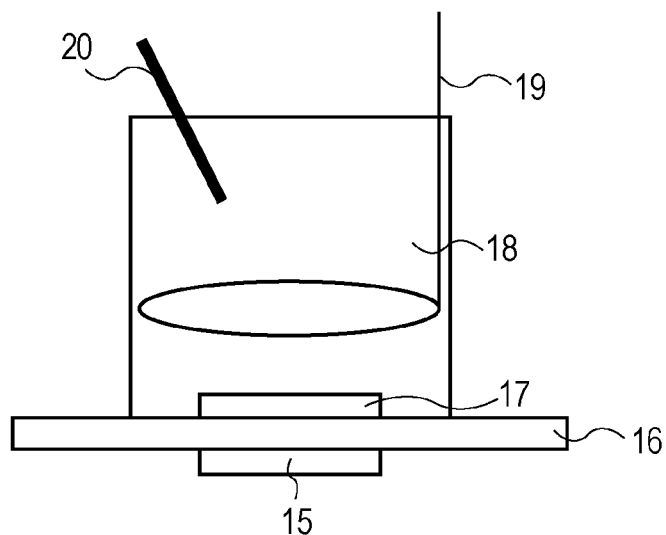
FIG. 19 is a schematic view showing a system of measurement used in cyclic voltammetry conducted for verifying the permeation-preventing effect of an electron mediator in the biofuel cell according to the second embodiment of the present invention.
Figure 20:
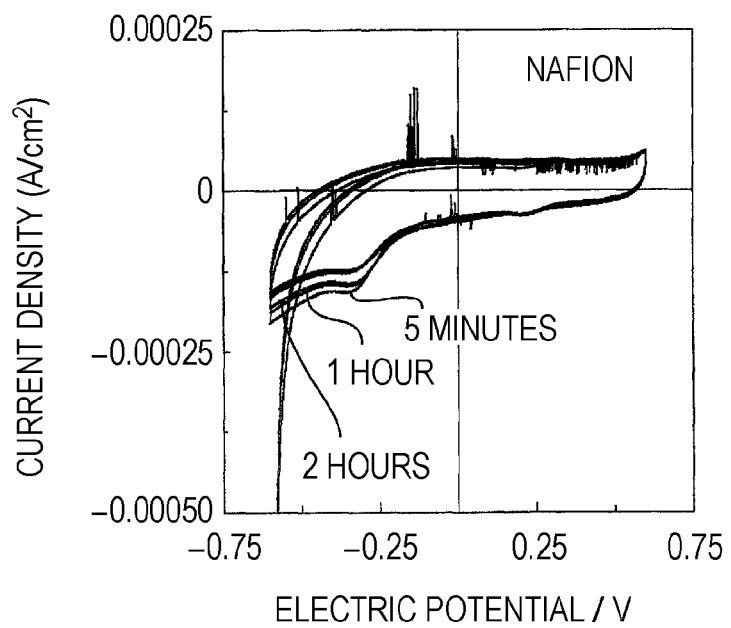
FIG. 20 is a schematic diagram showing the results of cyclic voltammetry conducted for verifying the permeation-preventing effect of an electron mediator in the biofuel cell according to the second embodiment of the present invention.
Figure 21:
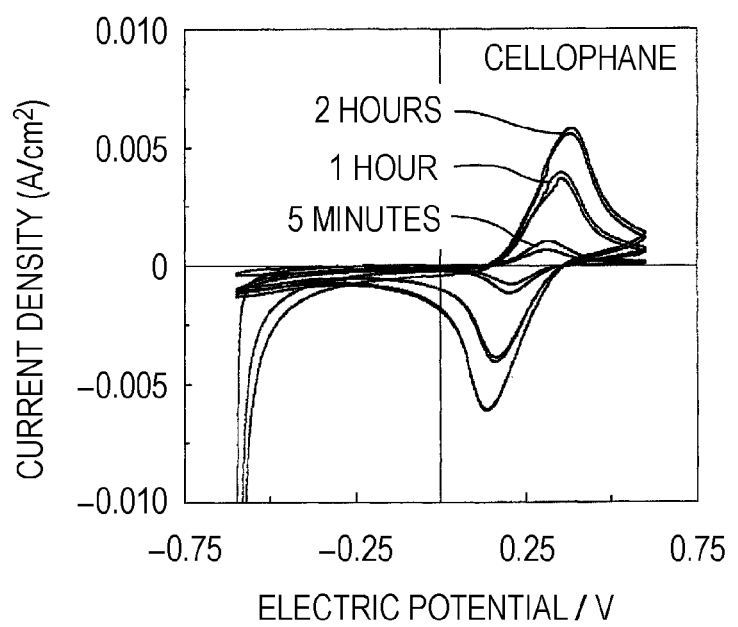
FIG. 21 is a schematic diagram showing the results of cyclic voltammetry conducted for verifying the permeation-preventing effect of an electron mediator in the biofuel cell according to the second embodiment of the present invention.

Next, commercially available carbon felt (manufactured by TORAY Industries Inc., B0050) was used as porous carbon. This carbon felt was cut into 1 cm squares. The carbon felt was impregnated with 80 μL of hexacyanoferrate ions (1 M) and then dried. Two electrodes thus prepared were overlapped and used as a test electrode. As shown in FIG. 19, a film-like separator 16 (corresponding to the electrolyte layer 3) was placed on the test electrode 15, and a working electrode 17 was provided so as to face the test electrode 15 with the separator 16 therebetween. Commercially available carbon felt (manufactured by TORAY Industries Inc., B0050) was cut into a 1 cm square and used as this working electrode 17. Furthermore, a solution prepared by dissolving hexacyanoferrate ions as an electron mediator in a buffer solution 18 composed of 0.4 M $NaH_2PO_4$/NaOH (pH 7) (where illustration of a container for placing the buffer solution 18 is omitted) was brought into contact with the separator 16 and the working electrode 17. Cellophane, which does not have an electric charge, and Nafion (pH 7), which is a polyanion having a negative electric charge, were used as the separator 16. Cyclic voltammetry was performed five minutes, one hour, and two hours after the contact of the separator 16 with the buffer solution 18 (electrolyte solution) in which hexacyanoferrate ions were dissolved to compare the value of oxidation-reduction peak of the electron mediator, i.e., hexacyanoferrate ions, that had passed from the test electrode 15 through the separator 16. A counter electrode 19 and a reference electrode 20 were immersed in the buffer solution 18, and an electrochemical measuring device (not shown) was connected to the working electrode 17, the counter electrode 19, and the reference electrode 20. A Pt wire was used as the counter electrode 19, and a Ag|AgCl was used as the reference electrode 20. The measurement was performed at the atmospheric pressure, and the measurement temperature was 25° C. FIG. 20 shows the measurement results in the case where Nafion was used as the separator 16. In addition, FIG. 21 shows the measurement results in the case where cellophane was used as the separator 16. As is understood from FIG. 21, in the case where cellophane was used as the separator 16, as soon as five minutes after the start of the measurement, an oxidation-reduction peak corresponding to hexacyanoferrate ions was observed, and the value of oxidation-reduction peak increased as the time elapsed. In contrast, as is understood from FIG. 20, in the case where Nafion was used as the separator 16, even after two hours had passed after the start of the measurement, no oxidation-reduction peak corresponding to hexacyanoferrate ions was observed. Accordingly, it was confirmed that when cellophane was used as the separator 16, hexacyanoferrate ions passed through the separator 16, but when Nafion was used as the separator 16, hexacyanoferrate ions did not pass through the separator 16.

According to this second embodiment, in addition to the same advantage as the first embodiment, the following advantage can be achieved. That is, since the electrolyte layer 3 has an electric charge having the same sign as the electric charge of an oxidized form or a reduced form of an electron mediator used in the cathode 2 and the anode 1, passing of one of electron mediators of the cathode 2 and the anode 1 through the electrolyte layer 3 and moving to the other one of the cathode 2 and the anode 1 can be effectively suppressed. Consequently, a decrease in the output and a decrease in the capacitance of the biofuel cell can be sufficiently suppressed.

Next, a biofuel cell according to a third embodiment of the present invention will be described.

Figure 23:
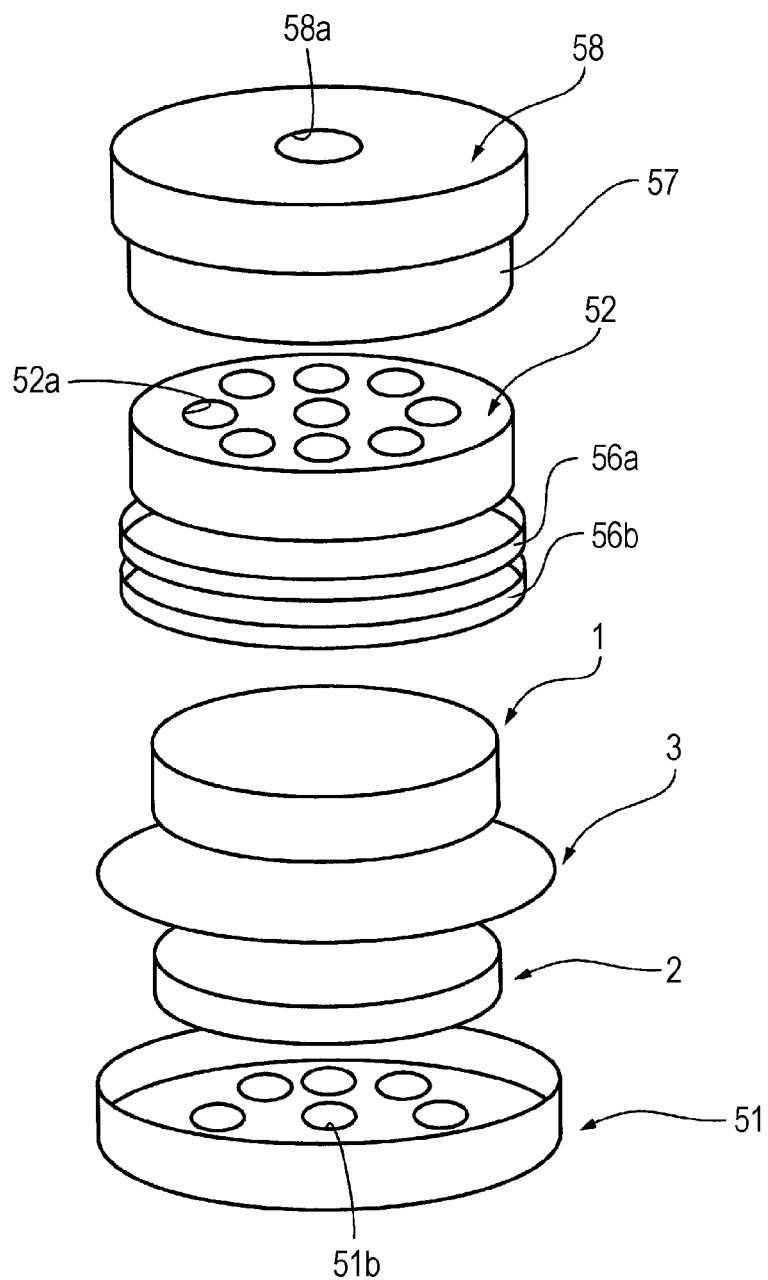
FIG. 23 is an exploded perspective view showing the biofuel cell according to the third embodiment of the present invention.

FIGS. 22(A), 22(B), and 22(C) and FIG. 23 show this biofuel cell. FIGS. 22(A), 22(B), and 22(C) are a top view, a cross-sectional view, and a rear surface view, respectively, of the biofuel cell. FIG. 23 is an exploded perspective view showing exploded individual components of the biofuel cell.

As shown in FIGS. 22(A), 22(B), and 22(C) and FIG. 23, in this biofuel cell, a cathode 2, an electrolyte layer 3, and an anode 1 are accommodated inside a space formed between a cathode current collector 51 and an anode current collector 52 so that the top and bottom thereof are sandwiched between the cathode current collector 51 and the anode current collector 52. Among the cathode current collector 51, the anode current collector 52, the cathode 2, the electrolyte layer 3, and the anode 1, adjacent components are in close contact with each other. In this case, the cathode current collector 51, the anode current collector 52, the cathode 2, the electrolyte layer 3, and the anode 1 each have a circular planar shape, and the biofuel cell also has a circular planer shape as a whole.

The cathode current collector 51 is configured to collect a current generated in the cathode 2, and the current is taken from this cathode current collector 51 to the outside. In addition, the anode current collector 52 is configured to collect a current generated in the anode 1. The cathode current collector 51 and the anode current collector 52 are generally composed of a metal or an alloy, but the material is not limited to this. The cathode current collector 51 is flat and has a substantially cylindrical shape. The anode current collector 52 is also flat and has a substantially cylindrical shape. Furthermore, the edge of an outer peripheral portion 51a of the cathode current collector 51 is caulked to an outer peripheral portion 52a of the anode current collector 52 with a ring-shaped gasket 56a compose of an insulating material, such as silicone rubber, and a ring-shaped hydrophobic resin 56b composed of, for example, polytetrafluoroethylene (PTFE) therebetween, thereby forming a space in which the cathode 2, the electrolyte layer 3, and the anode 1 are accommodated. The hydrophobic resin 56b is provided in the space surrounded by the cathode 2, the cathode current collector 51, and the gasket 56a so as to be in close contact with the cathode 2, the cathode current collector 51, and the gasket 56a. The hydrophobic resin 56b effectively suppresses excessive impregnation of a fuel to the cathode 2 side. The end of the electrolyte layer 3 extends outward from the cathode 2 and the anode 1 so as to be sandwiched between the gasket 56a and the hydrophobic resin 56b. The cathode current collector 51 has a plurality of oxidizing agent supply ports 51b provided over the entire surface of the bottom face thereof so that the cathode 2 is exposed in the oxidizing agent supply ports 51b. FIGS. 22(C) and 23 show thirteen circular oxidizing agent supply ports 51b, but this is only an example, and the number, the shape, the size, and the arrangement of oxidizing agent supply ports 51b may be appropriately selected. The anode current collector 52 also has a plurality of fuel supply ports 52b provided over the entire surface of the top face thereof so that the anode 1 is exposed in the fuel supply ports 52b. FIG. 23 shows seven circular fuel supply ports 52b, but this is only an example, and the number, the shape, the size, and the arrangement of fuel supply ports 52b may be appropriately selected.

The anode current collector 52 has a cylindrical fuel tank 57 provided on a surface opposite to the anode 1. The fuel tank 57 is formed integrally with the anode current collector 52. A fuel to be used (not shown), for example, a glucose solution, a glucose solution further containing an electrolyte, or the like is charged in the fuel tank 57. A cylindrical cover 58 is detachably provided on the fuel tank 57. The cover 58 is, for example, fitted into or screwed on the fuel tank 57. A circular fuel supply port 58a is formed at the center of the cover 58. The fuel supply port 58a is sealed by, for example, attaching a hermetic seal that is not shown in the figure.

The configuration of this biofuel cell other than the above-described configuration is the same as the first embodiment as long as the properties thereof are not adversely affected.

Next, an example of a method for manufacturing this biofuel cell will be described. FIGS. 24(A) to 24(D) show this manufacturing method.

Figure 24:
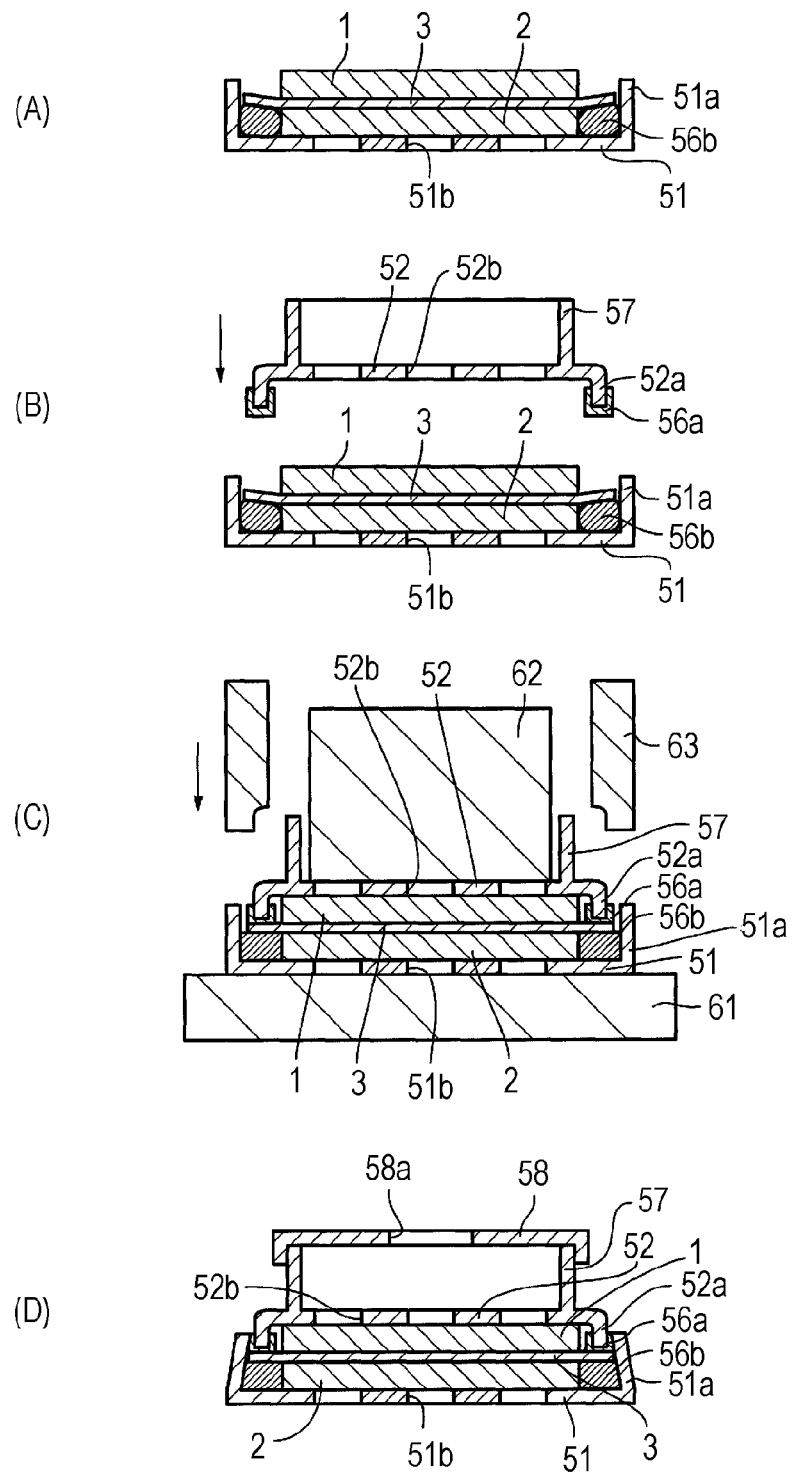
FIG. 24 includes schematic views illustrating a method for manufacturing the biofuel cell according to the third embodiment of the present invention.

As shown in FIG. 24(A), first, a cathode current collector 51 having a cylindrical shape with an open end is prepared. The cathode current collector 51 has a plurality of oxidizing agent supply ports 51b provided over the entire surface of the bottom face thereof. A ring-shaped hydrophobic resin 56b is placed on the outer peripheral portion of the inner bottom face of the cathode current collector 51, and a cathode 2, an electrolyte layer 3, and an anode 1 are sequentially stacked on the central portion of the bottom face.

Meanwhile, as shown in FIG. 24(B), an anode current collector 52 having a cylindrical shape with an open end and a fuel tank 57 formed integrally with the anode current collector 52 are prepared. The anode current collector 52 has a plurality of fuel supply ports 52b provided over the entire surface thereof. A gasket 56a having a U-shaped cross section is attached on the edge of the peripheral surface of the anode current collector 52. Furthermore, the anode current collector 52 is placed on the anode 1 so that the open end is located on the lower side, and the cathode 2, the electrolyte layer 3, and the anode 1 are sandwiched between the cathode current collector 51 and the anode current collector 52.

Next, as shown in FIG. 24(C), the cathode current collector 51 and the anode current collector 52 with the cathode 2, the electrolyte layer 3, and the anode 1 sandwiched therebetween are placed on a base 61 of a caulking machine, and the anode current collector 52 is pressed with a pressing member 62 to bring the cathode current collector 51, the cathode 2, the electrolyte layer 3, the anode 1, and the anode current collector 52 into close contact with adjacent ones. In this state, a caulking tool 63 is moved downward to caulk the edge of an outer peripheral portion 51a of the cathode current collector 51 to an outer peripheral portion 52a of the anode current collector 52 with the gasket 56a and the hydrophobic resin 56b therebetween. This caulking is performed such that the gasket 56a is gradually crushed so as not to form a clearance between the cathode current collector 51 and the gasket 56a and between the anode current collector 52 and the gasket 56a. Furthermore, in this case, the hydrophobic resin 56b is also gradually compressed so as to be brought into close contact with the cathode 2, the cathode current collector 51, and the gasket 56a. Consequently, a space for accommodating the cathode 2, the electrolyte layer 3, and the anode 1 is formed inside the cathode current collector 51 and the anode current collector 52 in a state in which the cathode current collector 51 and the anode current collector 52 are electrically insulated from each other through the gasket 56a. The caulking tool 63 is then moved upward.

Thus, as shown in FIG. 24(D), the biofuel cell is manufactured, in which the cathode 2, the electrolyte layer 3, and the anode 1 are accommodated in the space formed between the cathode current collector 51 and the anode current collector 52.

Next, a cover 58 is attached to the fuel tank 57, and a fuel and an electrolyte are injected from a fuel supply port 58a of the cover 58. The fuel supply port 58a is then closed by, for example, attaching a hermetic seal. However, the fuel and electrolyte may be injected into the fuel tank 57 in the step shown in FIG. 24(B).

In this biofuel cell, for example, when a glucose solution is used as the fuel to be charged in the fuel tank 57, on the anode 1, the supplied glucose is decomposed with the enzyme to produce electrons and to generate $H^+$. On the cathode 2, water is produced from $H^+$ transferred from the anode 1 through the electrolyte layer 3, the electrons transferred from the anode 1 through an external circuit, and oxygen in air, for example. As a result, an output voltage is produced between the cathode current collector 51 and the anode current collector 52.

Figure 25:
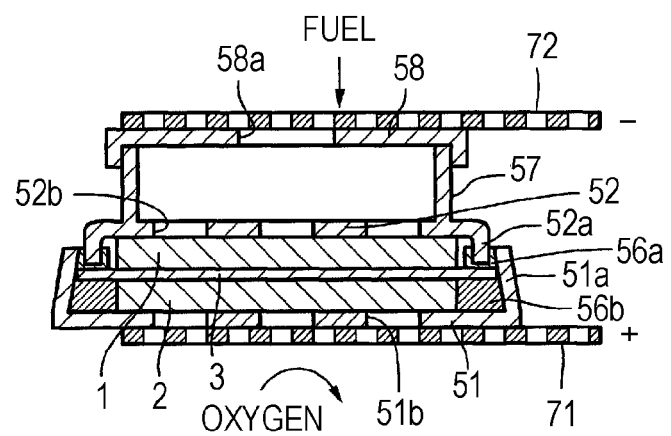
FIG. 25 is a schematic view illustrating a first example of a method for use of the biofuel cell according to the third embodiment of the present invention.

As shown in FIG. 25, mesh electrodes 71 and 72 may be formed on the cathode current collector 51 and the anode current collector 52, respectively, of this biofuel cell. In this case, outside air enters the oxidizing agent supply ports 51b of the cathode current collector 51 through holes of the mesh electrode 71, and a fuel enters the fuel tank 57 from the fuel supply port 58a of the cover 58 through holes of the mesh electrode 72.

Figure 26:
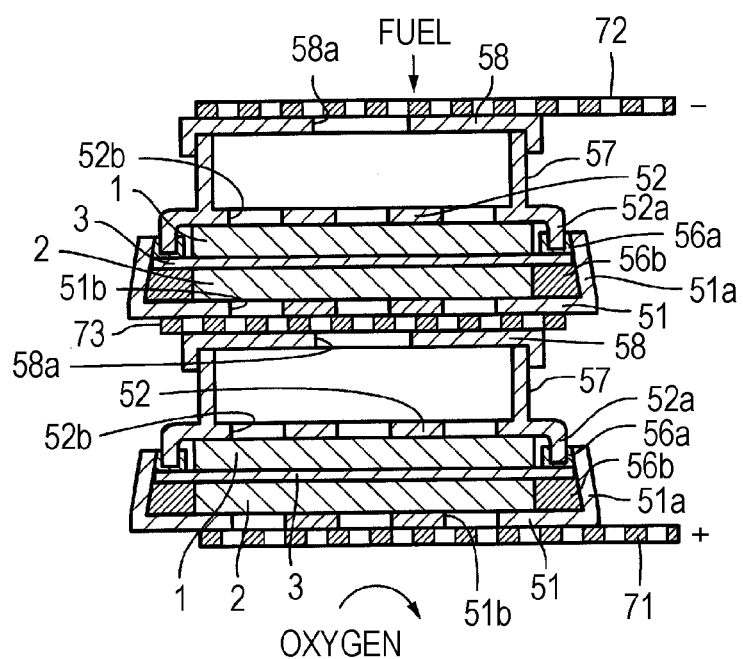
FIG. 26 is a schematic view illustrating a second example of a method for use of the biofuel cell according to the third embodiment of the present invention.

FIG. 26 shows a case in which two biofuel cells are connected in series. In this case, a mesh electrode 73 is sandwiched between the cathode current collector 51 of one (in the drawing, the upper biofuel cell) of the biofuel cells and the cover 58 of the other biofuel cell (in the drawing, the lower biofuel cell). In this case, outside air enters the oxidizing agent supply ports 51b of the cathode current collector 51 through holes of the mesh electrode 73. The fuel may be supplied using a fuel supply system.

FIG. 27 shows a case in which two biofuel cells are connected in parallel. In this case, the fuel tank 57 of one (in the drawing, the upper biofuel cell) of the two biofuel cells and the fuel tank 57 of the other biofuel cell (in the drawing, the lower biofuel cell) are brought into contact with each other so that the fuel supply ports 58a of the covers 58 coincide with each other, and an electrode 74 is lead from the side faces of these fuel tanks 57. In addition, mesh electrodes 75 and 76 are formed on the cathode current collector 51 of one of the biofuel cells and the cathode current collector 51 of the other biofuel cell, respectively. These mesh electrodes 75 and 76 are connected to each other. Outside air enters the oxidizing agent supply ports 51b of the cathode current collectors 51 through holes of the mesh electrodes 75 and 76.

According to the third embodiment, the same advantage as the first embodiment can be achieved in the coin-type or button-type biofuel cell excluding the fuel tank 57. Furthermore, in this biofuel cell, the cathode 2, the electrolyte layer 3, and the anode 1 are sandwiched between the cathode current collector 51 and the anode current collector 52, and the edge of the outer peripheral portion 51a of the cathode current collector 51 is caulked to the outer peripheral portion 52a of the anode current collector 52 with the gasket 56 therebetween. Accordingly, in this biofuel cell, the individual components can be uniformly bonded to each other, thereby preventing variation in the output and leakage of cell solutions such as the fuel and the electrolyte from the interfaces between the individual components. In addition, this biofuel cell is manufactured by a simple manufacturing process. In addition, this biofuel cell is easily reduced in size. Furthermore, in this biofuel cell, a glucose solution or starch is used as a fuel, and about pH 7 (neutrality) is selected as the pH of the electrolyte used. Accordingly, the biofuel cell is safe even if the fuel or the electrolyte leaks to the outside.

Furthermore, in air cells which are currently put into practical use, it is necessary to add a fuel and an electrolyte during manufacture, and thus it is difficult to add the fuel and the electrolyte after manufacture. In contrast, in this biofuel cell, since the fuel and the electrolyte may be added after manufacture, the biofuel cell can be manufactured easier than the air cells which are currently put into practical use.

Next, a biofuel cell according to a fourth embodiment of the present invention will be described.

As shown in FIG. 28, in the fourth embodiment, the fuel tank 57 provided integrally with the anode current collector 52 is removed from the biofuel cell according to the third embodiment, and in addition, the mesh electrodes 71 and 72 are provided on the cathode current collector 51 and the anode current collector 52, respectively. This biofuel cell is used in a state in which the fuel cell floats on a fuel 57a charged in an open fuel tank 57 so that the anode 1 is located on the lower side and the cathode 2 is located on the upper side.

The configuration of the fourth embodiment other than the above-described configuration is the same as the first and third embodiments as long as the properties thereof are not adversely affected.

According to the fourth embodiment, the same advantages as the first and third embodiments can be achieved.

Next, a biofuel cell according to a fifth embodiment of the present invention will be described. Whereas the biofuel cell according to the third embodiment is a coin type or a button type, this biofuel cell is a cylindrical type.

Figure 29:
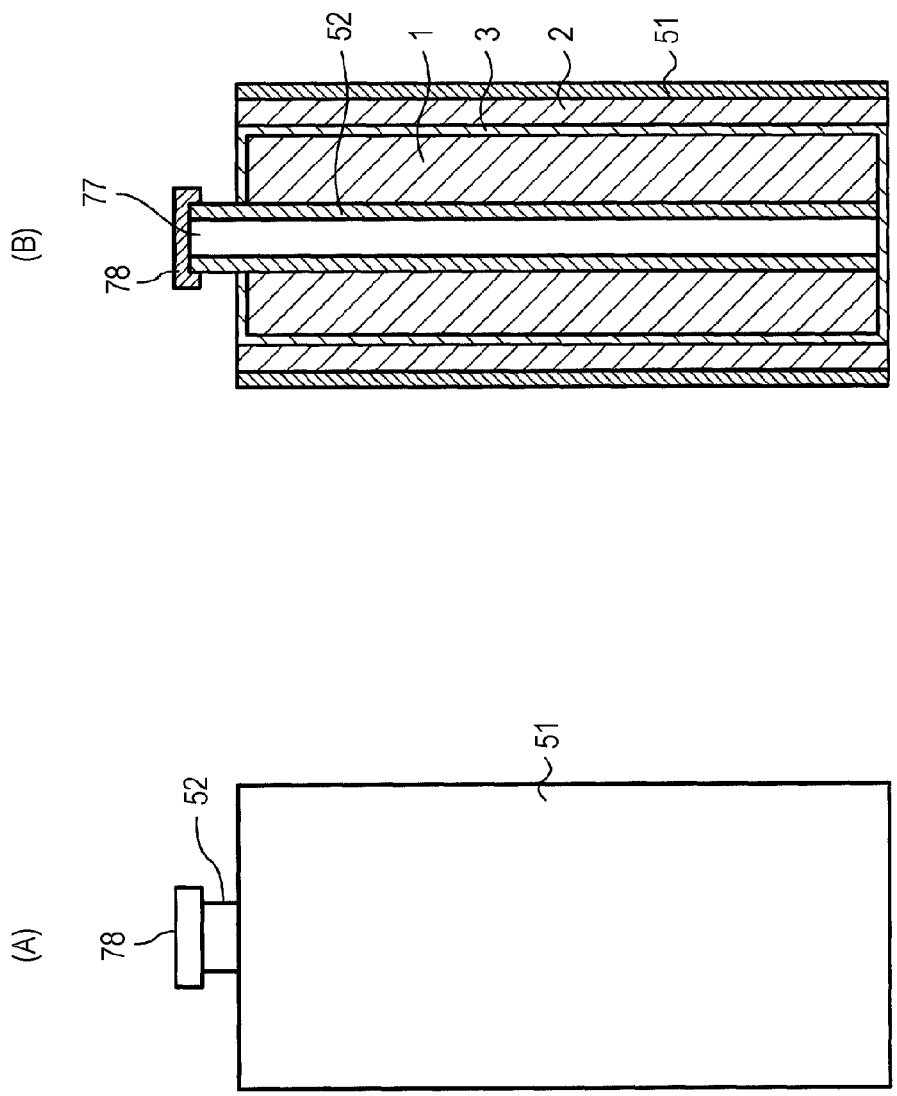
FIG. 29 includes a front view and a longitudinal cross-sectional view that show a biofuel cell according to a fifth embodiment of the present invention.
Figure 30:
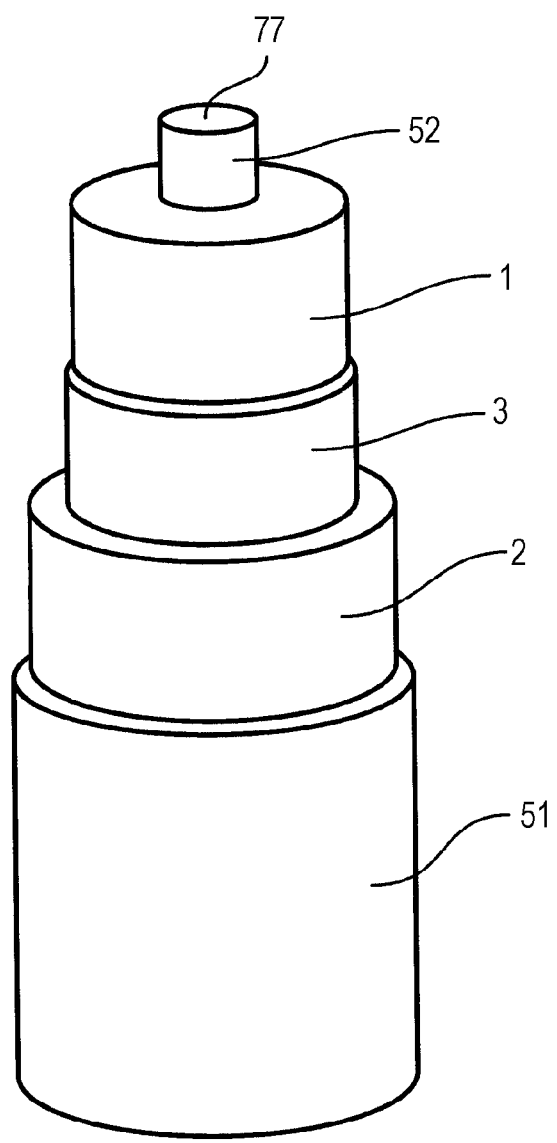
FIG. 30 is an exploded perspective view showing the biofuel cell according to the fifth embodiment of the present invention.

FIGS. 29(A) and 29(B) and FIG. 30 show the biofuel cell. FIG. 29(A) is a front view of the biofuel cell, FIG. 29(B) is a longitudinal cross-sectional view of the biofuel cell, and FIG. 30 is an exploded perspective view showing exploded individual components of the biofuel cell.

As shown in FIGS. 29(A) and 29(B) and FIG. 30, in this biofuel cell, an anode current collector 52, an anode 1, an electrolyte layer 3, a cathode 2, and a cathode current collector 51, each of which has a cylindrical shape, are sequentially provided on the outer periphery of a columnar fuel storage portion 77. In this case, the fuel storage portion 77 includes a space surrounded by the cylindrical anode current collector 52. An end of the fuel storage portion 77 projects outward, and a cover 78 is provided on the end. Although not shown in the figures, a plurality of fuel supply ports 52b are provided over the entire surface of the anode current collector 52 disposed on the outer periphery of the fuel storage portion 77. In addition, the electrolyte layer 3 has a bag shape that wraps the anode 1 and the anode current collector 52. The portion between the electrolyte layer 3 and the anode current collector 52 at an end of the fuel storage portion 77 is sealed with, for example, a sealing member (not shown) so that a fuel does not leak from this portion.

In this biofuel cell, a fuel and an electrolyte are charged in the fuel storage portion 77. The fuel and the electrolyte pass through the fuel supply ports 52b of the anode current collector 52, reach the anode 1, and permeate into pore portions of the anode 1 to be stored in the anode 1. In order to increase the amount of fuel that can be stored in the anode 1, the porosity of the anode 1 is preferably, for example, 60% or more, but is not limited to this.

In this biofuel cell, a gas-liquid separation layer may be provided on the outer peripheral surface of the cathode current collector 51 in order to improve durability. As the material for the gas-liquid separation layer, for example, a waterproof moisture-permeable material (a composite material of a stretched polytetrafluoroethylene film and a polyurethane polymer) (e.g., Gore-Tex (trade name) manufactured by W.L. Gore & Associates, Inc.) may be used. In order to uniformly bond the individual components of the biofuel cell to each other, preferably, stretchable rubber (which may be a band or a sheet) having a network structure through which air can pass from the outside is wound outside or inside the gas-liquid separation layer so that the whole components of the biofuel cell are fastened.

The configuration of the fifth embodiment other than the above-described configuration is the same as the first and third embodiments as long as the properties thereof are not adversely affected.

According to the fifth embodiment, the same advantages as the first and third embodiments can be achieved.

Next, a biofuel cell according to a sixth embodiment of the present invention will be described.

This biofuel cell uses starch, which is a polysaccharide, as a fuel. In addition, in association with the use of starch as the fuel, glucoamylase, which is a catabolic enzyme that decomposes starch into glucose, is also immobilized on an electrode 11 serving as an anode.

In this biofuel cell, when starch is supplied as the fuel to the anode 1 side, the starch is hydrolyzed into glucose with glucoamylase, and the glucose is decomposed with glucose dehydrogenase. Furthermore, $NAD^+$ is reduced in association with an oxidation reaction in this decomposition process to produce NADH, and the NADH is oxidized with diaphorase to be separated into two electrons, $NAD^+$, and $H^+$. Accordingly, two electrons and two $H^+$ are produced in a one-stage oxidation reaction per molecular of glucose. Four electrons and four $H^+$ in total are produced in a two-stage oxidation reaction. The electrons thus produced are transferred to the electrode 11 of the anode 1, and $H^+$ move to the cathode 2 through the electrolyte layer 3. On the cathode 2, the $H^+$ react with oxygen supplied from the outside and the electrons sent from the anode 1 through an external circuit to produce $H_2O$.

The configuration other than the above-described configuration is the same as the biofuel cell according to the first embodiment.

According to the sixth embodiment, the same advantage as the first embodiment can be achieved. In addition, since starch is used as the fuel, it is possible to achieve the advantage that the amount of electric power generated can be increased as compared with the case where glucose is used as a fuel.

The embodiments of the present invention have been specifically described above, but the present invention is not limited to the embodiments described above and various modifications can be made on the basis of the technical idea of the present invention.

For example, the numerical values, structures, configurations, shapes, materials, and the like described in the above embodiments are merely examples, and other numerical values, structures, configurations, shapes, materials, and the like, all of which are different from the above, may be used according to need.

According to the present invention, a fuel cell in which when an enzyme is immobilized on a cathode, a very high catalytic current value can be obtained in the cathode and a high current value can be stably obtained can be realized. Furthermore, high-performance electronic devices and the like can be realized by using this excellent fuel cell.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A fuel cell comprising a structure in which a cathode containing water and an anode face each other with a proton conductor therebetween,
    wherein an enzyme is immobilized on at least the cathode and the cathode has pores therein, and
    wherein a volume of water contained in the cathode is 70% or less of a volume of the pores of the cathode,
    wherein the proton conductor comprises an electrolyte containing an imidazole compound as a buffer substance, and
    wherein a dimyristoylphosphatidylcholine is immobilized on the anode.

2. The fuel cell according to claim 1, wherein an electron mediator is immobilized on the cathode.

3. The fuel cell according to claim 1, wherein the enzyme comprises an oxygen reductase immobilized on the cathode.

4. The fuel cell according to claim 3, wherein the oxygen reductase is bilirubin oxidase.

5. The fuel cell according to claim 1, wherein an enzyme is immobilized on the anode, and the enzyme comprises an oxidase that is immobilized on the anode and that accelerates oxidation of a monosaccharide and decomposes the monosaccharide.

6. The fuel cell according to claim 5, wherein the enzyme immobilized on the anode comprises a coenzyme oxidase that returns a coenzyme reduced in association with the oxidation of the monosaccharide to an oxidized form and that transfers an electron to the anode through an electron mediator.

7. The fuel cell according to claim 6, wherein the oxidized form of the coenzyme is NAD+ and the coenzyme oxidase is diaphorase.

8. The fuel cell according to claim 5, wherein the oxidase is NAD+-dependent glucose dehydrogenase.

9. A method for operating a fuel cell having a structure in which a cathode containing water and an anode face each other with a proton conductor therebetween, wherein an enzyme is immobilized on at least the cathode and the cathode has pores therein, the method comprising:
    controlling a volume of water contained in the cathode at 70% or less of a volume of the pores of the cathode,
    wherein the proton conductor comprises an electrolyte containing an imidazole compound as a buffer substance, and
    wherein dimyristoylphosphatidylcholine is immobilized on the anode.

10. An electronic device comprising one or a plurality of fuel cells,
    wherein the fuel cell has a structure in which a cathode containing water and an anode face each other with a proton conductor therebetween, wherein an enzyme is immobilized on at least the cathode and the cathode has pores therein;
    a volume of water contained in the cathode is 70% or less of a volume of the pores of the cathode,
    wherein the proton conductor comprises an electrolyte containing an imidazole compound as a buffer substance, and
    wherein dimyristoylphosphatidylcholine is immobilized on the anode.

11. The fuel cell according to claim 2, wherein the electron mediator is a compound having a quinone skeleton.

* * * * *